(12) United States Patent
Eary et al.

(10) Patent No.: US 9,790,206 B2
(45) Date of Patent: Oct. 17, 2017

(54) INTERMEDIATES FOR USE IN THE PREPARATION OF INDAZOLE DERIVATIVES AND PROCESSES FOR THE PREPARATION THEREOF

(71) Applicant: Array BioPharma Inc., Boulder, CO (US)

(72) Inventors: C. Todd Eary, Longmont, CO (US); Bruno P. Hache, Longmont, CO (US); Derrick Juengst, Boulder, CO (US); Stacey Renee Spencer, Lyons, CO (US); Peter J. Stengel, Irving, TX (US); Daniel John Watson, Lafayette, CO (US)

(73) Assignee: Array BioPharma Inc., Boulder, CO (US)

( * ) Notice: Subject to any disclaimer, the term of this patent is extended or adjusted under 35 U.S.C. 154(b) by 0 days.

(21) Appl. No.: 14/770,035

(22) PCT Filed: Feb. 27, 2014

(86) PCT No.: PCT/US2014/019039
§ 371 (c)(1),
(2) Date: Aug. 24, 2015

(87) PCT Pub. No.: WO2014/134313
PCT Pub. Date: Sep. 4, 2014

(65) Prior Publication Data
US 2016/0002210 A1    Jan. 7, 2016

Related U.S. Application Data

(60) Provisional application No. 61/770,031, filed on Feb. 27, 2013.

(51) Int. Cl.
*C07D 403/12* (2006.01)
*C07D 231/56* (2006.01)

(52) U.S. Cl.
CPC ......... *C07D 403/12* (2013.01); *C07D 231/56* (2013.01)

(58) Field of Classification Search
CPC .......................... C07D 403/12; C07D 231/56
See application file for complete search history.

(56) References Cited

U.S. PATENT DOCUMENTS

| | | | |
|---|---|---|---|
| 8,026,233 B2 * | 9/2011 | Munson ............... | C07D 401/12 514/212.08 |
| 8,039,639 B2 * | 10/2011 | Groneberg ........... | C07D 231/56 548/362.5 |
| 2010/0022529 A1 * | 1/2010 | Li ........................ | C07D 401/12 514/232.5 |

FOREIGN PATENT DOCUMENTS

| | | |
|---|---|---|
| WO | 2004078116 A2 | 9/2004 |
| WO | 2007089646 A1 | 8/2007 |
| WO | WO 2007089646 A1 * | 8/2007 ........... C07D 231/40 |

OTHER PUBLICATIONS

Cho, C.S. et al., Chem Commun., 2004, 104-105.
Komrokji, R. et al., Phase 1 dose-Escalation/Expansion Study of the p38/Tie2 Inhibitor ARRY-614 in Patients with IPSS Low/Int-1 Risk Myelodysplastic Syndromes ASH 2011, Abstract 118, 21 pages.
Lebedev, A.Y., et al., J. Org. Chem., 2005, 70, 596-602.
Lokhande, P.D., et al., Tetrahedron Letters, 2007, 48, 6890-6892.
Lukin, K., et al., J. Org. Chem. 2006, 71, 8166-8172.
Pabba, C. et al., Tetrahedron Letters, 2005, 46, 7553-7557.
Vina, D., et al., Organic Letters, 2007, 9(3), 525-528.
Watson, T.J., et al., Organic Process Research & Development, 2003, 7, 521-532.
Patent Cooperation Treaty, International Searching Authority, Search Report and Written Opinion for PCT/US2014/019039, 10 pages, Apr. 15, 2014.

* cited by examiner

*Primary Examiner* — Michael Barker
*Assistant Examiner* — Amanda L Aguirre
(74) *Attorney, Agent, or Firm* — Viksnins Harris Padys Malen LLP

(57) ABSTRACT

Provided herein are novel processes for preparing a compound of Formula (I) to the use of said compound as an intermediate in novel processes for the synthesis of indazole derivatives, and to indazole intermediates and derivatives prepared by the processes described herein.

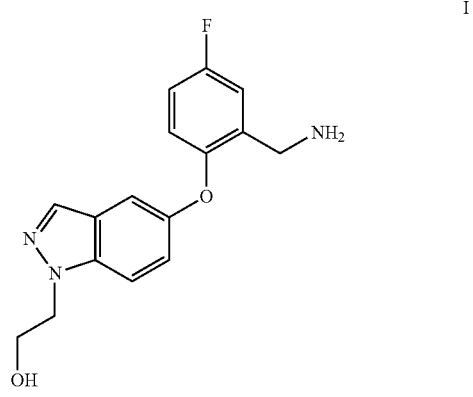

35 Claims, No Drawings

INTERMEDIATES FOR USE IN THE PREPARATION OF INDAZOLE DERIVATIVES AND PROCESSES FOR THE PREPARATION THEREOF

RELATED APPLICATIONS

This application is a 371 filing of PCT Application No. PCT/US2014/019039, filed Feb. 27, 2014, which claims priority to U.S. Provisional Application Ser. No. 61/770,031, filed Feb. 27, 2013, each of which is incorporated herein by reference in its entirety.

FIELD OF THE INVENTION

The present invention relates to novel processes for preparing a compound of Formula I

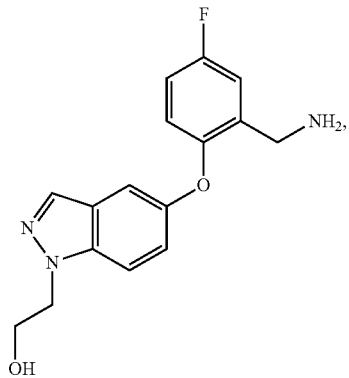

to the use of said compound as an intermediate in a novel process for the synthesis of indazole derivatives, and to indazole intermediates and derivatives prepared by the processes described herein.

DESCRIPTION OF THE STATE OF THE ART

Indazole derivatives have been described in WO 2004/078116 and WO 2007/089646. These compounds have inhibitory activity against the p38 MAPK protein kinase and therefore could be useful in the treatment of kinase-mediated conditions including proliferative disorders (such as myelodysplastic syndromes), inflammatory diseases, autoimmune diseases, destructive bone disorders, infectious diseases, viral diseases, fibrotic diseases and neurodegenerative diseases.

In particular, 1-(3-tert-butyl-1-p-tolyl-1H-pyrazol-5-yl)-3-(5-fluoro-2-(1-(2-hydroxyethyl)-1H-indazol-5-yloxy)benzyl)urea (hereinafter, "Compound A") is a known potent inhibitor of the p38 MAPK and Tie2 protein kinases and is useful in the treatment of hyperproliferative diseases, particularly cancer, in mammals. For example, in a recently published Phase 1 human clinical trial, Compound A demonstrated clinical activity as measured by hematologic improvement (increased neutrophils, platelets and/or red blood cells) in patients with myelodysplastic syndromes (MDS). In this Phase 1 dose-escalation/expansion study (N=45), Compound A demonstrated clinical activity as a single agent in patients with International Prognostic Scoring System (IPSS) Low or Intermediate-1 risk MDS and in whom treatments with approved therapies have failed, including hypomethylating agents and lenalidomide. A 38% response rate for hematologic improvement (HI) was observed in patients receiving drug at the highest dose, 1200 mg daily (n=16). At this dose, Compound A demonstrated multilineage HI in 67% of the responders, improving more than one cytopenia: neutropenia, thrombocytopenia and/or anemia. HI was demonstrated in 30% of all patients and generally increased with increasing total daily dose from 400 mg to 1200 mg (see, for example, R. Komrokji, et al., "Phase 1 Dose-Escalation/Expansion Study of the p38/Tie2 Inhibitor ARRY-614 in Patients with IPSS Low/Int-1 Risk Myelodysplastic Syndromes" 2011 Annual Meeting of the American Society of Hematology, Dec. 11, 2011; which can also be found at: http://www.arraybiopharma.com/_documents/Publication).

Compound A has the following general structure:

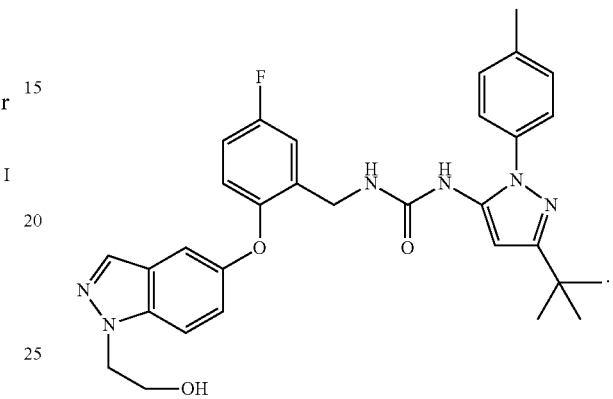

Compound A, as well as a process for its preparation, is disclosed in PCT Pub. No. WO 2007/089646. The manufacturing process described therein is, although suitable, regarded as disadvantageous for commercial production.

A key step in the synthesis of Compound A is the formation of the urea bond. For example, as reported in WO 2007/089646, Compound A may be prepared by reacting the key intermediate having the formula I

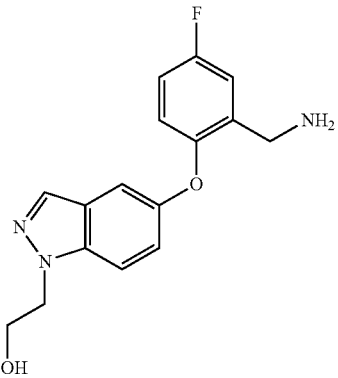

with a compound of formula II:

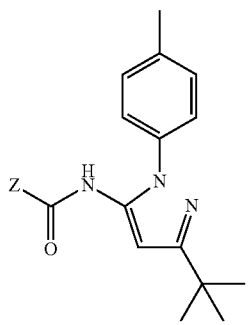

where Z represents a leaving group.

A process for preparing Intermediate I as reported in WO 2007/089646 involves a seven step process as shown in Scheme 1.

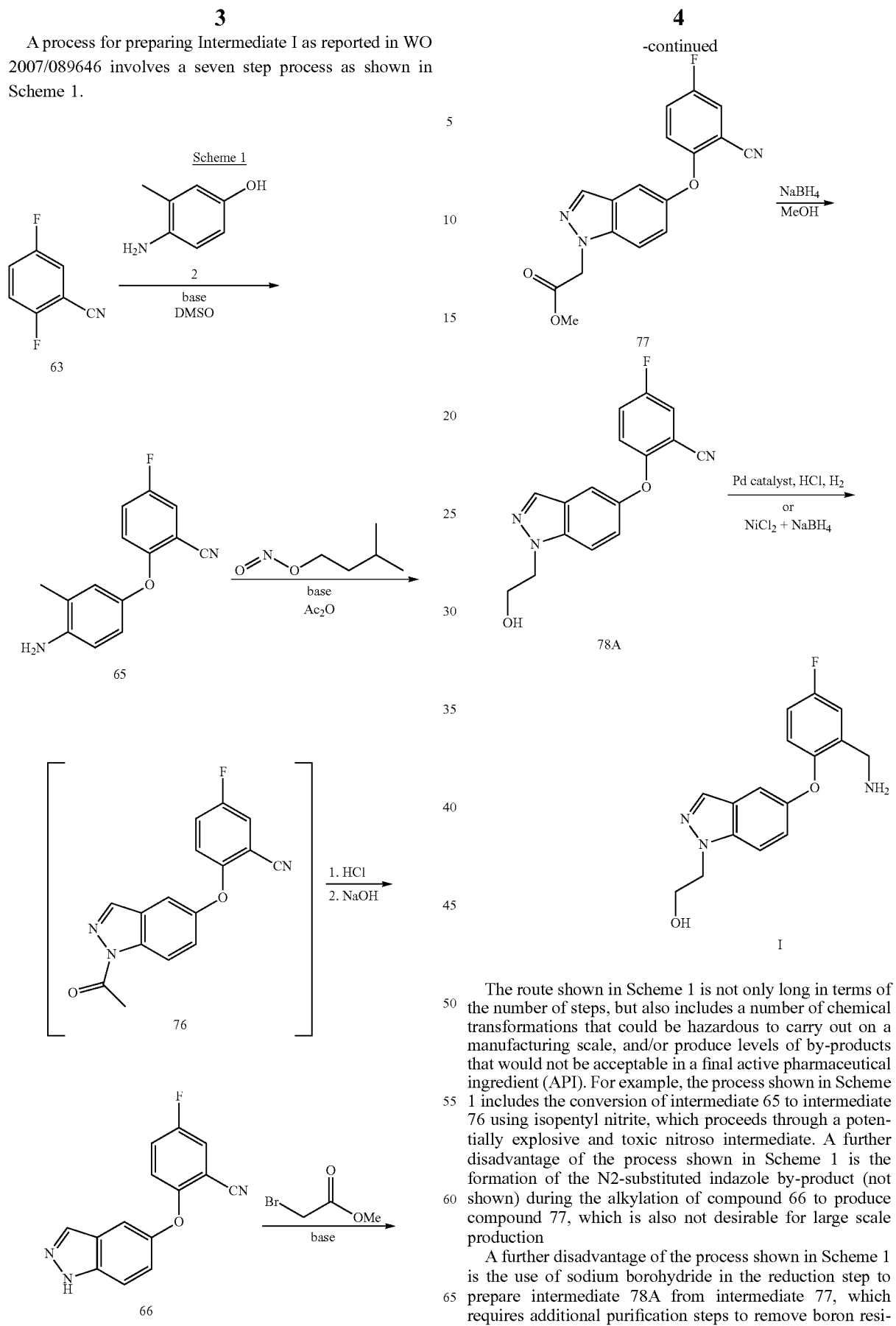

The route shown in Scheme 1 is not only long in terms of the number of steps, but also includes a number of chemical transformations that could be hazardous to carry out on a manufacturing scale, and/or produce levels of by-products that would not be acceptable in a final active pharmaceutical ingredient (API). For example, the process shown in Scheme 1 includes the conversion of intermediate 65 to intermediate 76 using isopentyl nitrite, which proceeds through a potentially explosive and toxic nitroso intermediate. A further disadvantage of the process shown in Scheme 1 is the formation of the N2-substituted indazole by-product (not shown) during the alkylation of compound 66 to produce compound 77, which is also not desirable for large scale production A further disadvantage of the process shown in Scheme 1 is the use of sodium borohydride in the reduction step to prepare intermediate 78A from intermediate 77, which requires additional purification steps to remove boron residues, which is not desirable for large scale production.

Due to the high potency of Compound A, in particular as a p38/Tie2 inhibitor, there is a need for improved manufacturing methods of this compound. In particular, there is a need to provide processes that fulfill one or more of the following criteria: scalable, safer; simpler; higher yielding and more economical when compared to known processes.

SUMMARY OF THE INVENTION

The present invention is directed to an improved process for the production of Compound A that is suitable for small scale or large scale manufacture, to novel intermediates useful for the preparation of Compound A, and to novel methods for the preparation of said intermediates.

In one embodiment, provided herein is an improved process for preparing an intermediate having the Formula I

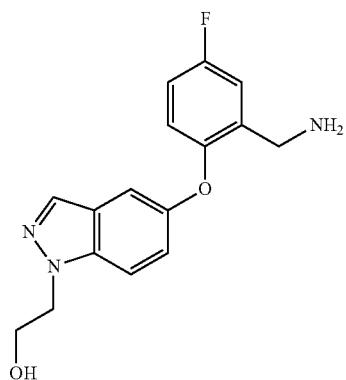

which is useful in the preparation of Compound A.

The processes provided herein for the preparation of the intermediate having the Formula I have at least the following advantages over the process reported in WO 2007/089646:

(1) the processes provided herein provide Intermediate I in fewer steps, thus decreasing labor and reagent costs, reducing the amount of waste, and increasing throughput;

(2) the processes provided herein for the preparation of Intermediate I avoid formation of a toxic and potentially explosive nitroso intermediate; and (3) fewer unwanted by-products are produced in the processes provided herein for the preparation of Intermediate I, thereby reducing the number of purification steps required.

Accordingly, the processes provided herein for the preparation of Intermediate I are more efficient than the known synthetic route and are more suitable for large-scale manufacture.

Also provided herein is an intermediate having the Formula I prepared by the processes described herein.

Also provided herein are novel processes for the synthesis of Compound A.

Also provided herein is Compound A prepared by the processes described herein.

DETAILED DESCRIPTION OF THE INVENTION

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable that is inherently discrete, the variable can be equal to any integer value of the numerical range, including the end-points of the range. Similarly, for a variable that is inherently continuous, the variable can be equal to any real value of the numerical range, including the end-points of the range. As an example, a variable that is described as having values between 0 and 2, can be 0, 1 or 2 for variables that are inherently discrete, and can be 0.0, 0.1, 0.01, 0.001, or any other real value for variables that are inherently continuous.

As used herein, the term "a %" or "area %" refers to the area in an HPLC chromatogram of one or more peaks compared to the total area of all peaks in the HPLC chromatogram expressed in percent of the total area.

In one embodiment, provided herein is a process for the preparation of a compound of Formula I

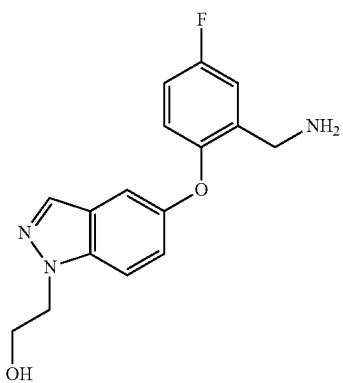

comprising:
(a) reacting a compound of formula (2)

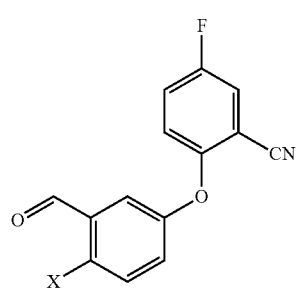

where X is Br or I, with 2-hydrazinylethanol in the presence of a base and a transition metal catalyst to provide a compound of formula (3)

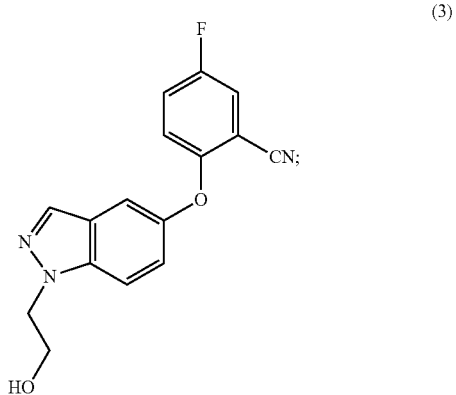

(3)

and (b) reducing the nitrile group of compound (3) to provide said compound of Formula I.

In one embodiment of step (a), a slight excess of 2-hydrazinylethanol is used. For example, in one embodiment about 1.05 to about 1.2 equivalents of 2-hydrazinylethanol are used. In one embodiment about 1.2 equivalents of 2-hydrazinylethanol are used.

Step (a) is performed in the presence of a suitable base. An example of a suitable base is an alkali metal carbonate, phosphate, hydride, alkoxide, bicarbonate or hydroxide. Examples include sodium carbonate, potassium carbonate, cesium carbonate, potassium phosphate, sodium hydride, potassium hydride, potassium tert-butoxide, sodium bicarbonate and sodium hydroxide. In one embodiment, the base used in step (a) is an alkali metal carbonate or an alkali metal phosphate. In one embodiment, the base used in step (a) is potassium carbonate. In one embodiment, step (a) utilizes about 1.0 to about 3.0 equivalents of a suitable base. In one embodiment, step (a) utilizes about two equivalents of base.

Step (a) may be performed in any suitable solvent or solvent system. Suitable solvents for step (a) include polar solvents, aprotic solvents, and polar, aprotic solvents.

In one embodiment, the solvent is a polar solvent. Examples include DMF, dimethylacetamide (DMA), 2,3,4,5-tetrahydrothiophene-1,1-dioxide (Sulfolane), N-methylpyrrolidone (NMP), THF, ethylene glycol dimethyl ether (DME), DMSO, acetone, acetonitrile, methanol, ethanol, isopropanol, n-propanol, t-butanol, and 2-methoxyethyl ether.

In one embodiment, the solvent is an aprotic solvent. Examples include acetonitrile, toluene, DMF, DMA, Sulfolane, NMP, diglyme, THF and DMSO.

In one embodiment, the solvent is a polar, aprotic solvent. Examples include DMF, DMA, Sulfolane, NMP, acetonitrile, diglyme, DMSO and THF.

In one embodiment, the solvent used in step (a) is DMSO, NMP, DMA or DMF.

In one embodiment, step (a) is performed at elevated temperatures, for example, between about 80 to about 140° C. In one embodiment, the reaction is performed at a temperature from about 100 to about 120° C.

Step (a) is performed in the presence of a suitable transition metal catalyst. In one embodiment, about 0.05 to 1 equivalents of the transition metal catalyst are used. In one embodiment, about 0.20 to 0.25 equivalents of the transition metal catalyst are used.

In general, the catalyst may be prepared from any transition metal, e.g., a metal selected from one of groups 3-12 of the periodic table or from the lanthanide series. In one embodiment, the transition metal is from Groups 5-12 of the periodic table. In one embodiment, the transition metal is from Groups 7-11 of the periodic table. In one embodiment, the transition metal catalyst is prepared from a metal selected from copper, platinum, palladium, iron, nickel, ruthenium or rhodium.

In one embodiment, the transition metal catalyst is a suitable copper catalyst, i.e., a suitable copper (I) and/or a copper (II) catalyst. Examples include $CuCO_3.Cu(OH)_2$, CuI, CuO, $CuBr_2$, $CuCO_3$, CuCl and $Cu_2O$. In one embodiment, step (a) utilizes between about 0.005 and about 0.20 to 0.25 equivalents of a copper catalyst. In one embodiment of step (a), the copper catalyst is $CuCO_3.Cu(OH)_2$.

In one embodiment when the transition metal catalyst is a copper catalyst, step (a) may be performed in the presence of both a copper catalyst and a diamine ligand. Examples of suitable diamine ligands include trans-1,2-bis(methylamino)cyclohexane and N,N'-dimethylethylene-diamine. In one embodiment, step (a) is performed in the presence of CuI as the catalyst and trans-1,2-bis(methylamino)cyclohexane as the ligand. In one embodiment, step (a) is performed in the presence of CuI or CuO as the catalyst and N,N'-dimethylethylene-diamine as the ligand.

In one embodiment, the transition metal catalyst is a suitable soluble palladium catalyst. Examples include tris(dibenzylideneacetone)dipalladium [$Pd_2(dba)_3$], bis(dibenzylideneacetone)palladium [$Pd(dba)_2$], palladium acetate and $PdCl_2$.

In certain embodiments, the palladium transition metal catalyst includes one or more phosphine or aminophosphine ligands. The phosphine ligands can be monodentate phosphine ligands, such as trimethylphosphine, triethylphosphine, tripropylphosphine, triisopropylphosphine, tributylphosphine, tricyclohexylphosphine, trimethyl phosphite, triethyl phosphite, tripropyl phosphite, triisopropyl phosphite, tributyl phosphite or tricyclohexyl phosphite; or a bidentate phosphine ligand such as 2,2'-bis(diphenylphosphino)-1,1'-binaphthyl (BINAP), 1,2-bis(dimethylphosphino)ethane, 1,2-bis(diethylphosphino)ethane, 1,2-bis(dipropylphosphino)-ethane, 1,2-bis(diisopropylphosphino)ethane, 1,2-bis(dibutyl-phosphino)ethane, 1,2-bis(dicyclohexylphosphino)ethane, 1,3-bis(dicyclohexylphosphino)propane, 1,3-bis(diisopropylphosphino)propane, 1,4-bis(diisopropylphosphino)-butane or 2,4-bis(dicyclohexylphosphino)pentane. The aminophosphines may be monodentate, e.g., each molecule of aminophosphine donates to the catalytic metal atom only a Lewis basic nitrogen atom or a Lewis basic phosphorus atom. Alternatively, the aminophosphine may be a chelating ligand, e.g., capable of donating to the catalytic metal atom both a Lewis basic nitrogen atom and a Lewis basic phosphorus atom.

In one embodiment, the transition metal catalyst is a suitable nickel catalyst. Examples include $Ni(acac)_2$, $NiCl_2[P(C_6H_5)]_2$, $Ni(1,5-cyclooctadiene)_2$, $Ni(1,10-phenanthroline)_2$, $Ni(dppf)_2$, $NiCl_2(dppf)$, $NiCl_2(1,10-phenanthroline)$, Raney nickel and the like, where "acac" represents acetylacetonate and "dppf" represents [1,1'-bis(diphenylphosphino)ferrocene].

Scheme 2 illustrates the preparation of compound (3) utilizing a copper catalyst as the transition metal catalyst under various reaction conditions as summarized in Table A. Scheme 2 further illustrates the hydrazone intermediate 2A (i.e., 2-(4-bromo-3-((2-(2-hydroxyethyl)hydrazono)methyl)phenoxy)-5-fluorobenzonitrile) and the by-product "dimer (a)" (i.e., 2-((1-(2-(3-cyano-4-((1-(2-hydroxyethyl)-1H-indazol-5-yl)oxy)phenoxy)ethyl)-1H-indazol-5-yl)oxy)-5-fluorobenzonitrile), which were identified in the crude reaction mixture of step (a). Table A provides the HPLC profile (area %) of the product, the intermediate hydrazine (2A), and the impurity (dimer a) observed for these comparative examples. For all examples summarized in Table A, step (a) was performed at 120° C. with the exception of Example 13, which was performed at reflux.

Scheme 2

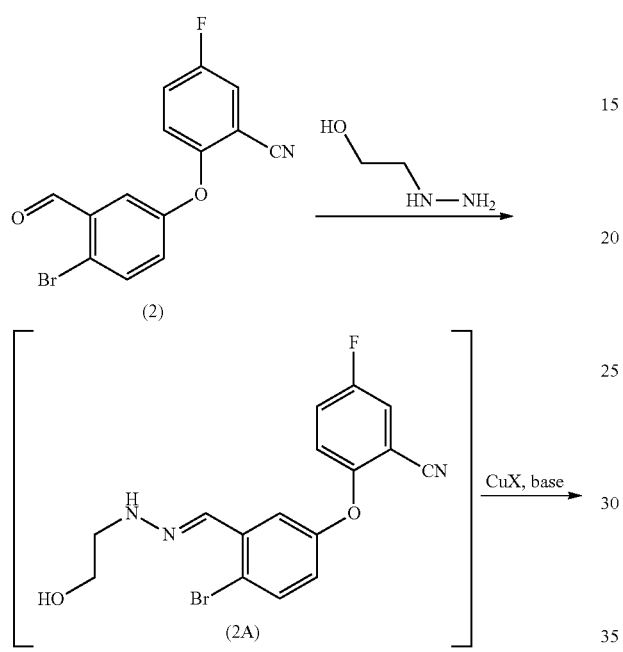

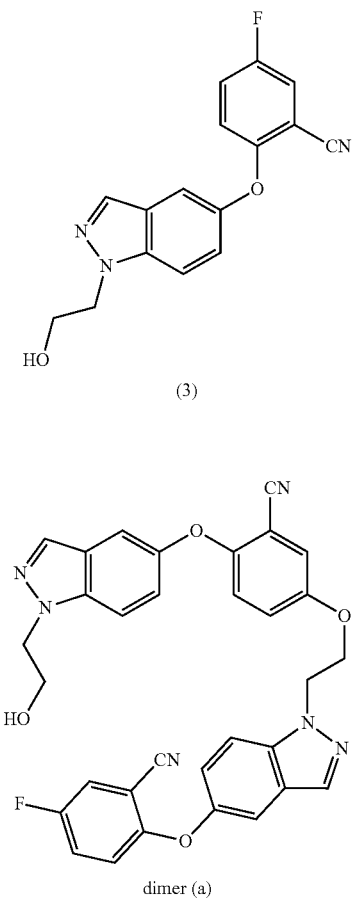

TABLE A

| Ex. | Cu catalyst | Equivs. of catalyst | Ligand | $K_2CO_3$ (equiv.) | Solvent | (3) HPLC[b] a % | (2A) HPLC[b] a % | dimer (a) HPLC[b] a % |
|---|---|---|---|---|---|---|---|---|
| 1 | CuI | 0.05 | A[c] | 2.0 | NMP | 81% | <1% | 2% |
| 2 | CuI | 0.05 | B[c] | 2.0 | NMP | 81% | 3% | 2% |
| 3 | CuI | 0.05 | none | 2.0 | NMP | 84% | 1% | 3% |
| 4 | CuO | 0.05 | B[c] | 2.0 | NMP | 68% | 2% | 2% |
| 5 | CuO | 0.05 | none | 2.0 | NMP | 65% | 1% | 1% |
| 6 | CuO[a] | 0.05 | A[c] | 2.0 | NMP | 82% | 1% | <1% |
| 7 | CuO[a] | 0.05 | B[c] | 2.0 | NMP | 84% | 2% | <1% |
| 8 | CuO[a] | 0.05 | none | 2.0 | NMP | 86% | 2% | <1% |
| 9 | CuCl | 0.02 | none | 2.0 | NMP | 75% | <1% | 3% |
| 10 | CuI | 0.05 | none | 2.0 | NMP | 72% | 1% | 10% |
| 11 | CuI | 0.05 | none | 2.0 | DMSO | 78% | 4% | <1% |
| 12 | CuI | 0.05 | none | 2.0 | Toluene | <5% | >90% | <1% |
| 13 | CuI | 0.05 | none | 2.0 | DMA | 86% | 1% | <1% |
| 14 | CuI | 0.02 | none | 1.5 | NMP | 73% | 4% | <1% |
| 15 | CuI | 0.02 | none | 3.0 | NMP | 85% | 1% | <1% |
| 16 | CuI | 0.02 | none | 2.0 | NMP | 84% | 2% | <1% |
| 17 | CuI | 0.01 | none | 2.0 | NMP | 84% | <1% | 2% |
| 18 | CuO[a] | 0.005 | none | 2.0 | DMA | 88% | 3% | <1% |
| 19 | CuO[a] | 0.005 | none | $Cs_2CO_3$ | DMA | 76% | 2% | 6% |
| 20 | CuO[a] | 0.005 | none | $K_3PO_4$ | DMA | 58% | 2% | 10% |
| 21 | $CuBr_2$ | 0.21 | none | 2.0 | DMA | 88% | 3% | <1% |
| 22 | CuO | 0.20 | none | 2.0 | DMA | 91% | 1% | 0.3% |
| 23 | $CuCO_3 \cdot Cu(OH)_2$ | 0.12 | none | 2.0 | DMA | 95% | 1% | <0.1% |

[a] nanopowder CuO
[b] HPLC a % in crude reaction mixture
[c] Ligand A: trans-1,2-bis(methylamino)cyclohexane; Ligand B: N,N'-dimethylethylene-diamine As shown in Table A, reactions conditions utilizing $CuCO_3.Cu(OH)_2$ as the copper catalyst produced higher amounts of intermediate (3) with lower amounts of intermediate (2A) and dimer (a) compared to the other copper catalysts listed in Table A. It was also observed that reactions utilizing $CuCO_3.Cu(OH)_2$ as the copper catalyst were about 20% faster compared to reaction using other copper catalysts.

Also as shown in Table A, the use of any of the copper catalysts in Table A as the transition metal catalyst does not require presence of a diamine ligand. Accordingly, in one embodiment step (a) utilizes a copper catalyst, wherein the reaction is performed in the absence of a diamine ligand. In one embodiment, the copper catalyst is $CuCO_3.Cu(OH)_2$, CuI, CuO, $CuBr_2$, $CuCO_3$, CuCl or $Cu_2O$. In one embodiment, the copper catalyst is $CuCO_3.Cu(OH)_2$.

Accordingly, in one embodiment step (a) comprises reacting a compound of formula (2)

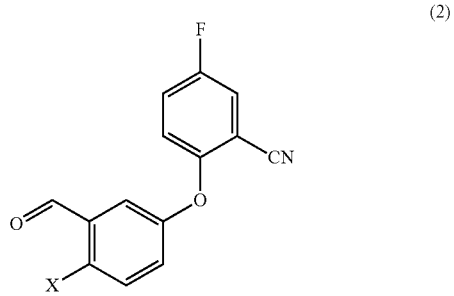

(2)

where X is Br or I, with 2-hydrazinylethanol in the presence of a catalytic amount of $CuCO_3.Cu(OH)_2$ and a base to provide a compound of formula (3)

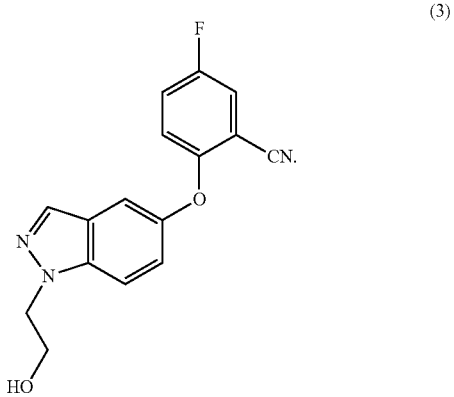 [SMILES: N#Cc1cc(F)ccc1Oc1ccc2c(cnn2CCO)c1]

(3)

In one embodiment of step (a), about 0.1 to 0.3 equivalents of $CuCO_3.Cu(OH)_2$ are used. In one embodiment of step (a), about 0.1 to 0.2 equivalents of $CuCO_3.Cu(OH)_2$ are used. In one embodiment of step (a), 0.20 to 0.25 equivalents of $CuCO_3.Cu(OH)_2$ are used. In one embodiment, about 1.05 to 1.2 equivalents of 2-hydrazinylethanol are used. In one embodiment, the base is an alkali metal carbonate, phosphate, hydride, alkoxide, bicarbonate or hydroxide. In one embodiment, the base is potassium carbonate.

A further advantage of the process described herein for the preparation of (3) is that step (a) directly provides the N1-substituted intermediate (3) from the substrate (2) in one step in a regioselective and chemoselective manner. In contrast, the method of WO 2007/089646 provides both the N1- and N2-substituted derivatives (see Representative Example A), which not only reduces the yield of the desired N1-substituted intermediate (77), but also requires an additional synthetic step and purification to isolate intermediate (3).

Step (b)

In one embodiment of step (b), the nitrile group of compound (3) is reduced under catalytic hydrogenation conditions or under non-catalytic hydrogenation conditions to provide the compound of Formula I.

Examples of reagents suitable for reducing a nitrile group under catalytic hydrogenation conditions include, but are not limited to Raney-type catalysts (such as Raney nickel catalysts (for example Raney Ni-MC700 and Raney Ni-MC703, supplied by Evonik Industries, and Raney cobalt catalysts), palladium catalysts (such as such as $Pd(OH)_2$ or palladium supported on carbon), and silicon-supported nickel/formic acid.

In one embodiment of step (b), the nitrile group of compound (3) is reduced under catalytic hydrogenation conditions using a Raney nickel catalyst. In one embodiment, the Raney nickel catalyst is Raney Ni-MC700 or Raney Ni-MC703.

In one embodiment of step (b), the nitrile group of compound (3) is reduced under catalytic hydrogenation conditions using any suitable palladium catalyst, such as $Pd(OH)_2$ or palladium supported on carbon. The catalytic hydrogenation when utilizing a palladium catalyst takes place under acidic conditions (such as by the addition of an acid, for example HCl or acetic acid) or with the addition of ammonia.

The catalytic hydrogenation of the nitrile group step (b) can be carried out in any suitable solvent or solvent system. Examples of suitable solvents include alcohols (e.g., methanol, ethanol, or isopropanol), esters (e.g., ethyl acetate) or ethers (e.g., THF). Suitable solvent systems include any combination of suitable solvents, such as a combination of an alcohol and THF.

In one embodiment, the hydrogen pressure in step (b) when using catalytic hydrogenation conditions is in the range of from about 25 to about 200 psi, for example 40 psi. The catalytic hydrogenation is typically performed at a temperature between 20-100° C.

Examples of reagents suitable for reducing a nitrile group under non-catalytic hydrogenation conditions include, but are not limited to, nickel boride, $NaBH_4$—$BF_3$ and borane-dimethylsulfide.

In one embodiment of step (b), the nitrile group is reduced using nickel boride in a suitable organic solvent such as an alcohol to provide the intermediate compound having Formula I. In one embodiment, the nickel boride can be prepared in situ from a transition metal salt, such as a Ni(II) salt, and sodium borohydride. For example, in one embodiment, the nickel boride is prepared from nickel (II) chloride and sodium borohydride. In one embodiment the reaction is performed in a suitable solvent such as an alcohol (e.g., methanol, ethanol or isopropanol). In one embodiment the reaction is performed at ambient temperature.

In one embodiment of step (b), the nitrile group of compound (3) is reduced under catalytic hydrogenation conditions using from about 5% to 20% of a Raney nickel catalyst in the presence of ammonia. In one embodiment, from about 5% to about 10% of the Raney nickel catalyst is used. In one embodiment, the Raney nickel catalyst is Raney Ni-MC700 or Raney Ni-MC703. The use of Raney Ni- MC700 or Raney Ni-MC703 as the catalyst in the nitrile reduction step (b) was found to have several advantages over the nickel boride reduction method. For example, catalytic hydrogenation conditions using Raney Ni-MC700 or Raney Ni-MC703 as the catalyst provided a higher yield of Formula I than the nickel boride reduction conditions, with an isolated yield of Formula I of 75-85% compared to an isolated yield of Formula I of 60-70% for the nickel-boride reduction.

In addition, fewer unwanted by-products were observed when the nitrile group of compound (3) was reduced under catalytic hydrogenation conditions using Raney Ni-MC700 or Raney Ni-MC703 as the catalyst compared to the number and levels of by-products (b), (c), (d) and (e) produced under nickel-boride reduction conditions as shown in Scheme 3 (see also Representative Example B).

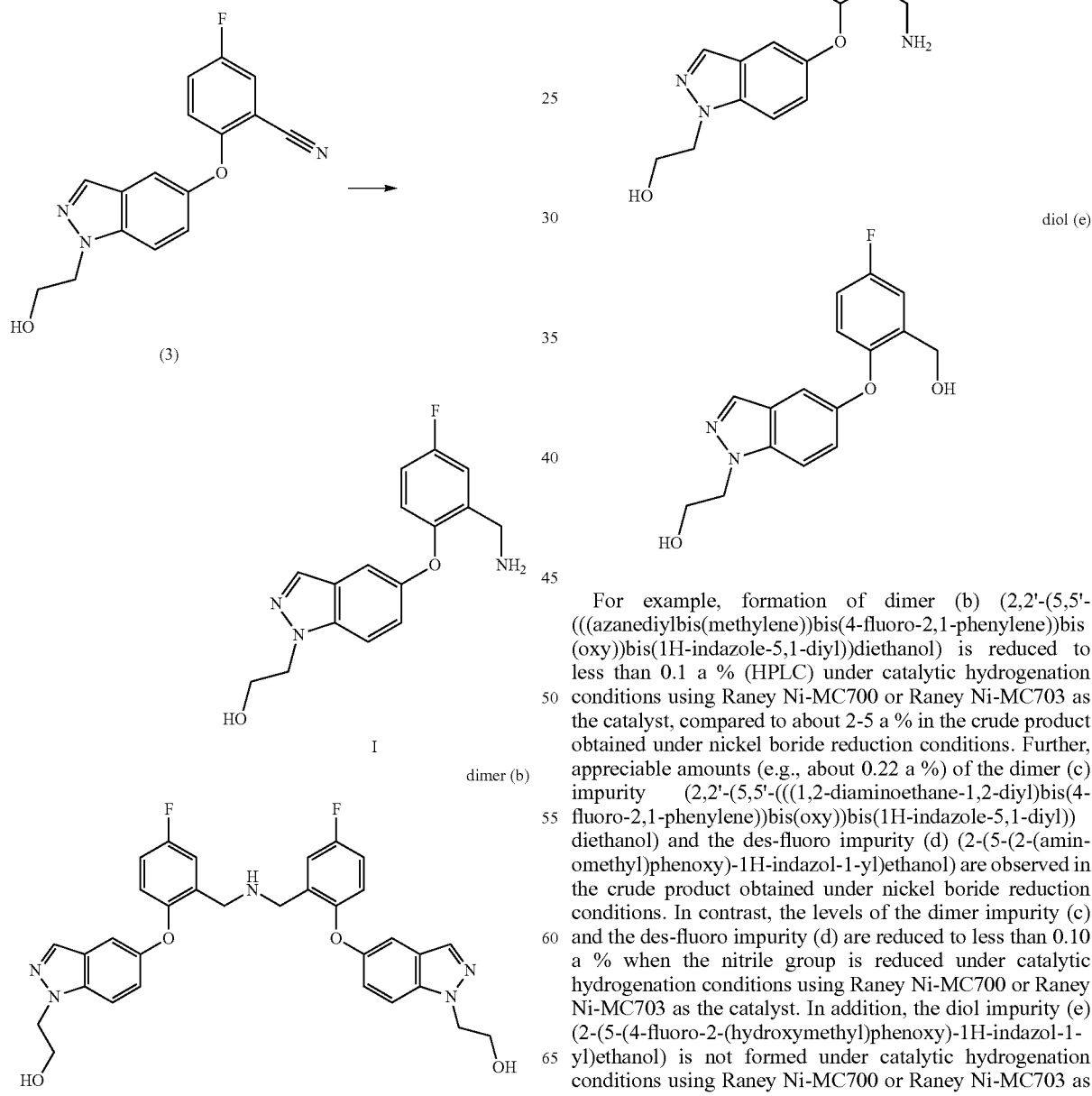

For example, formation of dimer (b) (2,2'-(5,5'-(((azanediylbis(methylene))bis(4-fluoro-2,1-phenylene))bis(oxy))bis(1H-indazole-5,1-diyl))diethanol) is reduced to less than 0.1 a % (HPLC) under catalytic hydrogenation conditions using Raney Ni-MC700 or Raney Ni-MC703 as the catalyst, compared to about 2-5 a % in the crude product obtained under nickel boride reduction conditions. Further, appreciable amounts (e.g., about 0.22 a %) of the dimer (c) impurity (2,2'-(5,5'-(((1,2-diaminoethane-1,2-diyl)bis(4-fluoro-2,1-phenylene))bis(oxy))bis(1H-indazole-5,1-diyl))diethanol) and the des-fluoro impurity (d) (2-(5-(2-(aminomethyl)phenoxy)-1H-indazol-1-yl)ethanol) are observed in the crude product obtained under nickel boride reduction conditions. In contrast, the levels of the dimer impurity (c) and the des-fluoro impurity (d) are reduced to less than 0.10 a % when the nitrile group is reduced under catalytic hydrogenation conditions using Raney Ni-MC700 or Raney Ni-MC703 as the catalyst. In addition, the diol impurity (e) (2-(5-(4-fluoro-2-(hydroxymethyl)phenoxy)-1H-indazol-1-yl)ethanol) is not formed under catalytic hydrogenation conditions using Raney Ni-MC700 or Raney Ni-MC703 as the catalyst, whereas about 1-5% of the diol impurity (e) is obtained in the crude product obtained under nickel boride reduction conditions. Controlling the levels of these downstream impurities in the synthesis of Compound A is desirable. Since the impurity levels are so low when the nitrile group is reduced under catalytic hydrogenation conditions using Raney Ni-MC700 or Raney Ni-MC703 as the catalyst, these reaction conditions obviate the need to perform an aqueous work-up as is required when using nickel boride nitrile conditions. This improvement dramatically streamlines the process and minimizes the waste stream.

Accordingly, in one embodiment step (b) comprises reducing the nitrile group of compound (3) under catalytic hydrogenation conditions using Raney Nickel as the catalyst in the presence of ammonia to provide said compound of Formula I. In one embodiment, the Raney nickel catalyst is Raney Ni-MC700 or Raney Ni-MC703.

In one embodiment, the compound of formula (2) can be prepared by the process comprising:

(a1) reacting a compound of formula (1)

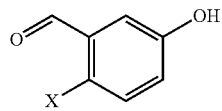

where X is Br or I, with 2,5-difluorobenzonitrile in the presence of a base to provide a compound of formula (2)

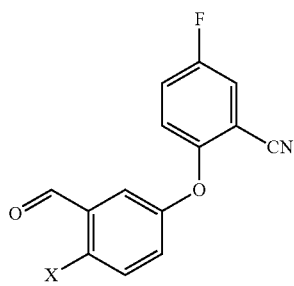

where X is Br or I.

In one embodiment, step (a1) utilizes about two to five equivalents of 2,5-difluorobenzonitrile. In one embodiment, step (a1) utilizes about two equivalents of 2,5-difluorobenzonitrile.

In one embodiment, step (a1) is performed in the presence of a suitable base. Examples of suitable bases include inorganic bases such as alkali metal carbonates, hydrides and bicarbonates. Examples include sodium carbonate, potassium carbonate, cesium carbonate, sodium hydride, and sodium bicarbonate. Other suitable bases include potassium fluoride and sodium hydroxide.

The reaction of a compound of formula (1) with 2,5-difluorobenzonitrile is performed in a suitable solvent. Examples of suitable solvents include DMSO, DMF, NMP, acetonitrile, dioxane, DME and Sulfolane.

In one embodiment, the preparation of compound (2) from compound (1) is performed at elevated temperatures, for example, from about 70° C. up to about 120° C. In one embodiment, step (a1) is performed at a temperature from about 80° C. to about 100° C. In one embodiment, step (a1) is performed at about 80° C.

In one embodiment, provided herein is a process for preparing a compound of Formula I, comprising:

(a1) reacting a compound of formula (1)

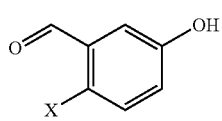

where X is Br or I, with 2,5-difluorobenzonitrile in the presence of a base to provide a compound of formula (2)

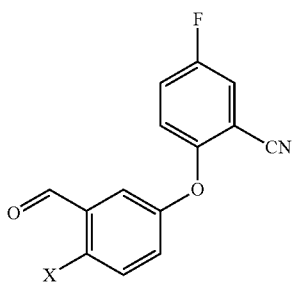

where X is Br or I;

(a) reacting said compound of formula (2) with 2-hydrazinylethanol in the presence of a base and a transition metal catalyst to provide a compound of formula (3)

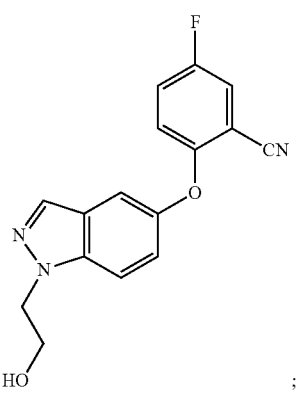

and (b) reducing the nitrile group of compound (3) to provide said compound of Formula I.

In one embodiment of the above process, about 2-3 equivalents of 2,5-difluorobenzonitrile are used.

In one embodiment of the above process, about 1.05 to about 1.2 equivalents of 2-hydrazinylethanol are used.

In one embodiment of the above process, the transition metal catalyst is a copper catalyst. In one embodiment of the above process, the transition metal catalyst is CuCO$_3$.Cu(OH)$_2$.

Examples of bases suitable for step (a) include alkali metal carbonates, alkali metal phosphates, alkali metal hydrides, alkali metal alkoxides, alkali metal bicarbonates, alkali metal hydroxides, and ammonia.

In one embodiment of the above process, the base used in step (a) is an alkali metal carbonate, phosphate, hydride, alkoxide, bicarbonate or hydroxide. In one embodiment, the base is an alkali metal carbonate or an alkali metal phosphate.

In one embodiment of the above process, the base used in step (a) is ammonia.

In one embodiment of the above process, the nitrile group is reduced under catalytic hydrogenation conditions. In one embodiment, the catalyst is a Raney Nickel catalyst. In one embodiment, the catalyst is Raney Ni-MC700 or Raney Ni-MC703.

Also provided herein is a compound of Formula I, prepared by the process comprising:

(a) reacting a compound of formula (2)

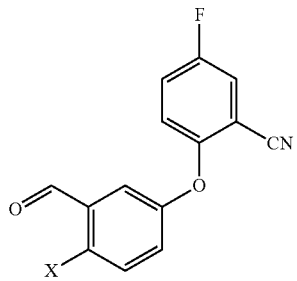
(2)

where X is Br or I, with 2-hydrazinylethanol in the presence of a base and a transition metal catalyst to provide a compound of formula (3)

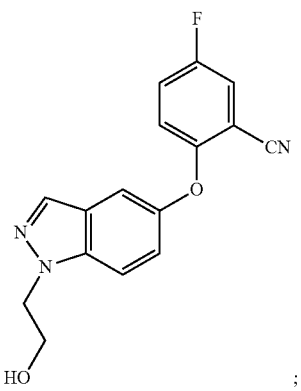
(3)

and (b) reducing the nitrile group of compound (3) to provide said compound of Formula I.

In one embodiment of the above process, about 1.05 to about 1.2 equivalents of 2-hydrazinylethanol are used.

In one embodiment of the above process, the transition metal catalyst is a copper catalyst. In one embodiment of the above process, the transition metal catalyst is CuCO$_3$.Cu(OH)$_2$.

In one embodiment of the above process, the base used in step (a) is an alkali metal carbonate, phosphate, hydride, alkoxide, bicarbonate or hydroxide. In one embodiment, the base is an alkali metal carbonate or an alkali metal phosphate.

In one embodiment of the above process, the nitrile group is reduced under catalytic hydrogenation conditions. In one embodiment, the catalyst is a Raney Nickel catalyst. In one embodiment, the catalyst is Raney Ni-MC700 or Raney Ni-MC703.

Also provided herein is a compound of Formula I, prepared by the process comprising:

(a1) reacting a compound of formula (1)

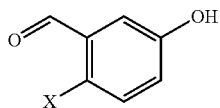
(1)

where X is Br or I, with 2,5-difluorobenzonitrile in the presence of a base to provide a compound of formula (2)

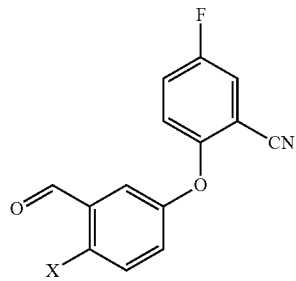
(2)

where X is Br or I;

(a) reacting said compound of formula (2) with 2-hydrazinylethanol in the presence of a transition metal catalyst and a base to provide a compound of formula (3)

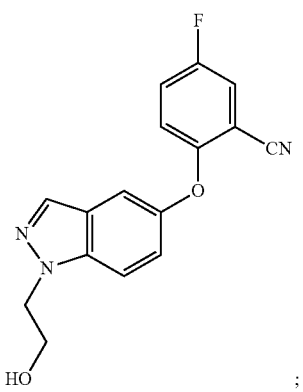
(3)

and (b) reducing the nitrile group of compound (3) to provide said compound of Formula I.

In one embodiment of the above process, about 2-3 equivalents of 2,5-difluorobenzonitrile are used.

In one embodiment of the above process, about 1.05 to about 1.2 equivalents of 2-hydrazinylethanol are used.

In one embodiment of the above process, the transition metal catalyst is a copper catalyst. In one embodiment of the above process, the transition metal catalyst is CuCO$_3$.Cu(OH)$_2$.

In one embodiment of the above process, the base used in step (a) is an alkali metal carbonate, phosphate, hydride, alkoxide, bicarbonate or hydroxide. In one embodiment, the base is an alkali metal carbonate or an alkali metal phosphate.

In one embodiment of the above process, the nitrile group is reduced under catalytic hydrogenation conditions. In one embodiment, the catalyst is a Raney Nickel catalyst. In one embodiment, the catalyst is Raney Ni-MC700 or Raney Ni-MC703.

In one embodiment, the compound of Formula I, when prepared by any of the above described processes and when the nitrile group of compound (3) is reduced under catalytic hydrogenation conditions using Raney Ni-MC700 or Raney Ni-MC703 as the catalyst, contains less than 0.1a % of the impurity "dimer (b)" (2,2'-(5,5'-(((azanediylbis(methylene))bis(4-fluoro-2,1-phenylene))bis(oxy))bis(1H-indazole-5,1-diyl))diethanol) as determined by HPLC.

In one embodiment, the compound of Formula I, when prepared by any of the above processes and when the nitrile group of compound (3) is reduced under catalytic hydrogenation conditions using Raney Ni-MC700 or Raney Ni-MC703 as the catalyst, contains less than 0.1a % of impurity "dimer (c)" (2,2'-(5,5'-(((1,2-diaminoethane-1,2-diyl)bis(4-fluoro-2,1-phenylene))bis(oxy))bis(1H-indazole-5,1-diyl))diethanol) as determined by HPLC.

In one embodiment, the compound of Formula I, when prepared by any of the above processes and when the nitrile group of compound (3) is reduced under catalytic hydrogenation conditions using Raney Ni-MC700 or Raney Ni-MC703 as the catalyst, contains less than 0.1a % of the impurity "des-fluoro (d)" (2-(5-(2-(aminomethyl)phenoxy)-1H-indazol-1-yl)ethanol) as determined by HPLC.

In one embodiment, the compound of Formula I, when prepared by any of the above processes and when the nitrile group of compound (3) is reduced under catalytic hydrogenation conditions using Raney Ni-MC700 or Raney Ni-MC703 as the catalyst, contains less than 0.1a %, of the impurity "diol (e)" (2-(5-(4-fluoro-2-(hydroxymethyl)phenoxy)-1H-indazol-1-yl)ethanol) as determined by HPLC. That is, the amount of impurity "diol (e)", if present, was below the detection limit of the instrument used to analyze the product.

In one embodiment, the compound of Formula I is useful in the preparation of Compound A.

Accordingly, also provided herein is a process for preparing Compound A having the formula

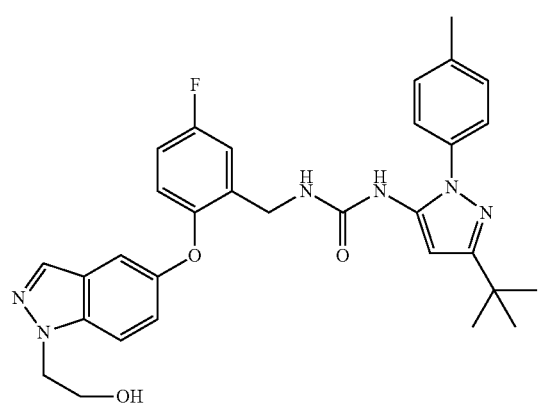 [SMILES: Cc1ccc(-n2nc(C(C)(C)C)cc2NC(=O)NCc2cc(F)ccc2Oc2ccc3c(cnn3CCO)c2)cc1]

comprising:

(a) reacting a compound of formula (2)

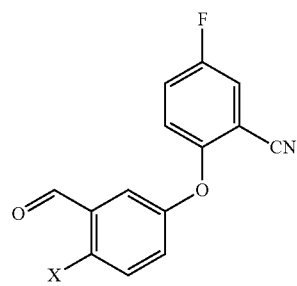

where X is Br or I, with 2-hydrazinylethanol in the presence of a base and a transition metal catalyst to provide a compound of formula (3)

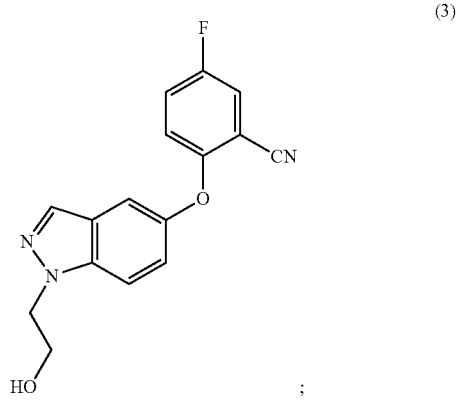 [SMILES: N#Cc1cc(F)ccc1Oc1ccc2c(cnn2CCO)c1]

(b) reducing the nitrile group of compound (3) to provide a compound of Formula I

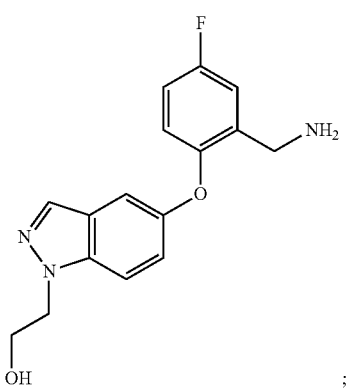

(c) coupling said compound of Formula I with a compound of formula (4)

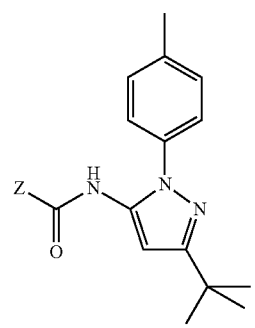

where Z represents a leaving group, to provide Compound A; and (d) optionally treating the product of Step (d) with HCl to isolate Compound A as the monohydrochloride salt.

In one embodiment of the process for preparing Compound A, the compound having the formula (2) is prepared by (a1) reacting a compound of formula (1)

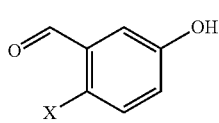
(1)

where X is Br or I, with 2,5-difluorobenzonitrile in the presence of a base to provide said compound having the formula (2). In one embodiment, about 2 equivalents of 2,5-difluorobenzonitrile are used.

In one embodiment of the above process for preparing Compound A, about 1.05 to about 1.2 equivalents of 2-hydrazinylethanol are used.

In one embodiment of the above process for preparing Compound A, step (a1) is performed in the presence of a base selected from alkali metal carbonates, hydrides and bicarbonates.

In one embodiment of the above process for preparing Compound A, the transition metal catalyst is a copper catalyst. In one embodiment of the above process, the copper catalyst is $CuCO_3 \cdot Cu(OH)_2$.

In one embodiment of the above process for preparing Compound A, the base used in step (a) is an alkali metal carbonate, phosphate, hydride, alkoxide, bicarbonate or hydroxide. In one embodiment, the base is an alkali metal carbonate or an alkali metal phosphate.

In one embodiment of the above process for preparing Compound A, the nitrile group is reduced under catalytic hydrogenation conditions. In one embodiment, the catalyst is a Raney Nickel catalyst. In one embodiment, the catalyst is Raney Ni-MC700 or Raney Ni-MC703.

In one embodiment of the above process for preparing Compound A, the leaving group in step (c) represented by Z may be, for example a halo(1-6C)alkoxy group, such as 2,2,2-trichloroethoxy, an alkenyloxy group such as $CH_2=C(CH_3)O-$, or an aryloxy group wherein said aryl portion is optionally substituted, for example, with one or more groups independently selected from F, Cl, Br, and $NO_2$. Particular values for an optionally substituted aryloxy group include phenoxy, 4-chlorophenoxy, 4-bromophenoxy, 4-fluorophenoxy, 4-nitrophenoxy, and 2-nitrophenoxy. In a particular embodiment, Z is phenoxy.

In one embodiment of the above process for preparing Compound A, the coupling of a compound of Formula I with a compound of formula (4) when Z is an optionally substituted phenoxy group can be performed at a temperature between 0 and 100° C., and more particularly at ambient temperature. Suitable solvents include 2-propanol (IPA) and aprotic solvents such as ethers (for example THF or p-dioxane), DMF, DMSO or acetonitrile. The coupling reaction is optionally performed in the presence of a base such as a tertiary amine (for example, triethylamine or DMAP).

The above described process for preparing Compound A optionally further includes the step (d) which comprises treating the free base of Compound A formed in Step (c) with at least one equivalent of HCl to isolate the monohydrochloride salt of Compound A.

In one embodiment, steps (c) and (d) are performed in 2-propanol, which allows for the isolation of the hydrochloride salt without the need for an aqueous workup.

Also provided herein is Compound A prepared by the process comprising:
(a) reacting a compound of formula (2)

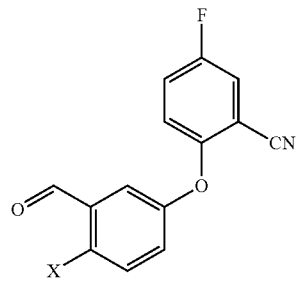
(2)

where X is Br or I, with 2-hydrazinylethanol in the presence of a base and a transition metal catalyst to provide a compound of formula (3)

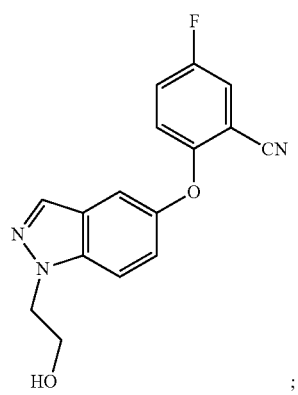
(3)

;

(b) reducing the nitrile group of compound (3) to provide a compound of Formula I

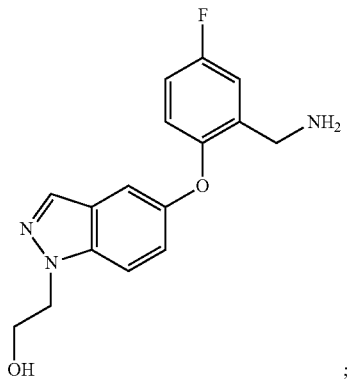
I

;

(c) coupling said compound of Formula I with a compound of formula (4)

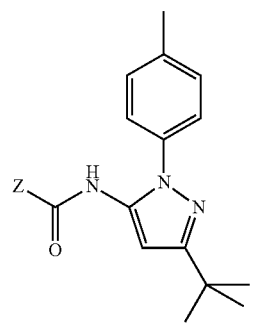
(4)

where Z represents a leaving group, to provide Compound A; and (d) optionally treating the product of Step (d) with HCl to isolate Compound A as the monohydrochloride salt.

In one embodiment of the above process, about 1.05 to about 1.2 equivalents of 2-hydrazinylethanol are used.

In one embodiment of the above process, the transition metal catalyst is a copper catalyst. In one embodiment of the above process, the copper catalyst is $CuCO_3 \cdot Cu(OH)_2$.

In one embodiment of the above process, the base used in step (a) is an alkali metal carbonate, phosphate, hydride, alkoxide, bicarbonate or hydroxide. In one embodiment, the base is an alkali metal carbonate or an alkali metal phosphate.

In one embodiment of the above process, the nitrile group is reduced under catalytic hydrogenation conditions. In one embodiment, the catalyst is a Raney Nickel catalyst. In one embodiment, the catalyst is Raney Ni-MC700 or Raney Ni-MC703.

In one embodiment of the above process, the leaving group in step (c) represented by Z is a halo(1-6C)alkoxy group, such as 2,2,2-trichloroethoxy, an alkenyloxy group such as $CH_2=C(CH_3)O—$, or an aryloxy group wherein said aryl portion is optionally substituted, for example, with one or more groups independently selected from F, Cl, Br, and $NO_2$. In one embodiment, Z is phenoxy, 4-chlorophenoxy, 4-bromophenoxy, 4-fluorophenoxy, 4-nitrophenoxy, and 2-nitrophenoxy. In a particular embodiment, Z is phenoxy.

In one embodiment of the above process, the coupling of a compound of Formula I with a compound of formula (4) when Z is an optionally substituted phenoxy group can be performed at a temperature between 0 and 100° C., and more particularly at ambient temperature. Suitable solvents include alcohols, such as 2-propanol (IPA), and aprotic solvents such as ethers (for example THF or p-dioxane), DMF, DMSO or acetonitrile. The coupling reaction is optionally performed in the presence of a base such as a tertiary amine (for example, triethylamine or DMAP).

Also provided herein is Compound A prepared by the process comprising:

(a1) reacting a compound of formula (1)

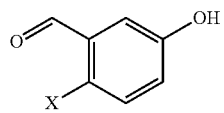

(1)

where X is Br or I, with 2,5-difluorobenzonitrile in the presence of a base to provide a compound having the formula (2)

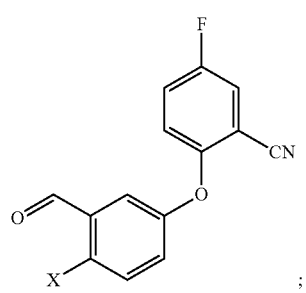

(2)

(a) reacting said compound of formula (2) with 2-hydrazinylethanol in the presence of a base and a transition metal catalyst to provide a compound of formula (3)

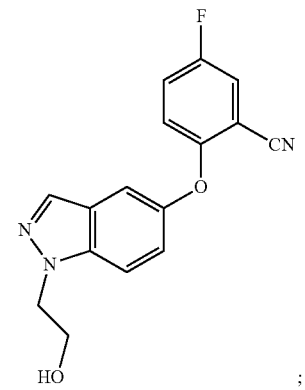

(3)

(b) reducing the nitrile group of compound (3) to provide a compound of Formula I

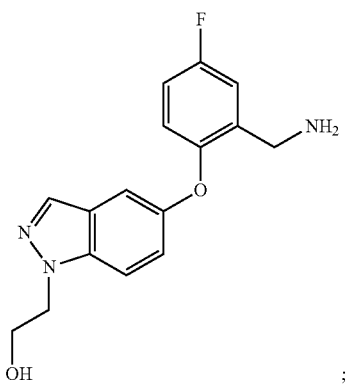

I (c) coupling said compound of Formula I with a compound of formula (4)

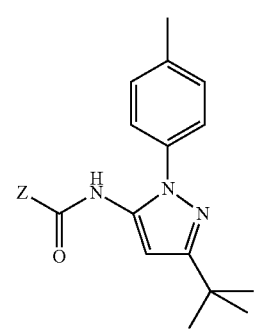

(4)

where Z represents a leaving group, to provide Compound A; and (d) optionally treating the product of step (d) with HCl to isolate Compound A as the monohydrochloride salt.

In one embodiment of the above process, about 1.05 to about 1.2 equivalents of 2-hydrazinylethanol are used.

In one embodiment of the above process, step (a1) is performed in the presence of a base selected from alkali metal carbonates, hydrides and bicarbonates.

In one embodiment of the above process, the transition metal catalyst is a copper catalyst. In one embodiment of the above process, the copper catalyst is CuCO$_3$.Cu(OH)$_2$.

In one embodiment of the above process, the base used in step (a) is an alkali metal carbonate, phosphate, hydride, alkoxide, bicarbonate or hydroxide. In one embodiment, the base is an alkali metal carbonate or an alkali metal phosphate.

In one embodiment of the above process, the nitrile group is reduced under catalytic hydrogenation conditions. In one embodiment, the catalyst is a Raney Nickel catalyst. In one embodiment, the catalyst is Raney Ni-MC700 or Raney Ni-MC703.

In one embodiment of the above process, the leaving group in step (c) represented by Z is a halo(1-6C)alkoxy group, such as 2,2,2-trichloroethoxy, an alkenyloxy group such as CH$_2$=C(CH$_3$)O—, or an aryloxy group wherein said aryl portion is optionally substituted, for example, with one or more groups independently selected from F, Cl, Br, and NO$_2$. In one embodiment, Z is phenoxy, 4-chlorophenoxy, 4-bromophenoxy, 4-fluorophenoxy, 4-nitrophenoxy, and 2-nitrophenoxy. In a particular embodiment, Z is phenoxy.

In one embodiment of the above process, the coupling of a compound of Formula I with a compound of formula (4) when Z is an optionally substituted phenoxy group can be performed at a temperature between 0 and 100° C., and more particularly at ambient temperature. Suitable solvents include alcohols, such as 2-propanol (IPA), and aprotic solvents such as ethers (for example THF or p-dioxane), DMF, DMSO or acetonitrile. The coupling reaction is optionally performed in the presence of a base such as a tertiary amine (for example, triethylamine or DMAP).

The processes described herein provide Intermediate I in fewer steps compared to the process reported in WO 2007/089646, which describes a seven step synthesis of intermediate I. In addition, the process described herein provides Intermediate I with reduced levels of impurities compared to the process reported in WO 2007/089646. In addition, step (a) for producing compound (3) avoids proceeding through the isopentyl nitrite diazonium chemistry used in WO 2007/089646 (see conversion of 65 to 76 in Scheme 1), thereby avoiding formation of a carcinogenic and potentially explosive intermediate. The process described herein also provides a higher overall yield of intermediate I compared to WO 2007/089646.

EXAMPLES

The following examples illustrate the invention. In the examples described below, unless otherwise indicated all temperatures are set forth in degrees Celsius. Reagents were purchased from commercial suppliers such as Aldrich Chemical Company, Lancaster, Alfa, Aesar, TCI, Maybridge, Chemik, Nanjing Chemlin, Merck, Alfa Aesar or other suitable suppliers, and were used without further purification unless otherwise indicated. Solvents were purchased from EMD, Macron/Mallinckrodt or Pharmco-Aaper and used as received.

Example 1

Preparation of 2-(5-(2-(aminomethyl)-4-fluorophenoxy)-1H-indazol-1-yl)ethanol

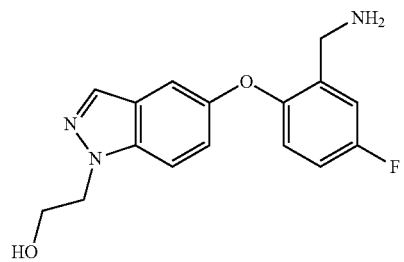 [SMILES: NCc1cc(F)ccc1Oc1ccc2c(cnn2CCO)c1]

Step (a1): Preparation of 2-(4-bromo-3-formylphenoxy)-5-fluorobenzonitrile

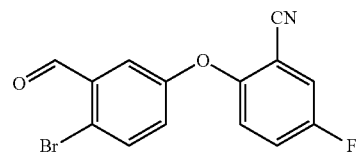 [SMILES: N#Cc1cc(F)ccc1Oc1ccc(Br)c(C=O)c1]

2-Bromo-5-hydroxybenzaldehyde (350 g, 1741 mmol, 1.0 equivalent), 2,5-difluorobenzonitrile (484 g, 3482 mmol, 2.0 equivalents) and potassium carbonate 325 mesh (253 g, 1828 mmol, 1.05 eq.) were added to a round bottom flask outfitted with a mechanical stirrer, temperature probe, reflux condenser and N$_2$ adaptor for positive N$_2$ pressure. DMSO (1.75 L) was added under stirring. The mixture was warmed to 80-90° C. and after 3-4 hour the reaction mixture was monitored by HPLC (HPLC conditions: 20 µL in a mixture of 8 mL CH$_3$CN and 2 mL water; 2-Bromo-5-hydroxybenzaldehyde, 2-(4-bromo-3-formylphenoxy)-5-fluorobenzonitrile, and 2,5-difluorobenzonitrile. When the reaction was complete (as determined by HPLC), the heat source was removed and the reaction was gradually cooled to <10° C. 2-Propanol (3.5 L) was added to the mixture and then water (3.5 L) was added at a rate such that the internal temperature stayed <20° C. A sticky solid formed at the start of the water addition which then became free-flowing as more water was added. The mixture was stirred at about 10° C. for 2 hours and then filtered (polypropylene cloth). The filtrate contained about 4 g of 2-(4-bromo-3-formylphenoxy)-5-fluorobenzonitrile (<1%). The solid was washed with water (2×3.5 L) and dried in a vacuum oven at 55° C. to give 528 g of bromo-3-formylphenoxy)-5-fluorobenzonitrile that was 95.0 wt %. (Purity can be further enhanced by performing a recrystallization in a minimal amount of dichloroethane).

Step (a): Preparation of 5-fluoro-2-((1-(2-hydroxyethyl)-1H-indazol-5-yl)oxy)benzonitrile To a 2 L round-bottomed flask was added 2-hydrazinylethanol (24.1 mL, 356 mmol, 1.2 eq.), 2-(4-bromo-3-formylphenoxy)-5-fluorobenzonitrile (100 g, 296 mmol, 1.0 eq.), and DMA (300 mL). The mixture was heated to 120° C. for 45 minutes. Formation of the hydrazone intermediate was deemed complete when there was less than 5 a % of bromo-3-formylphenoxy)-5-fluorobenzonitrile remaining. In a separate flask was added potassium carbonate 325 mesh (82.0 g, 594 mmol), CuCO$_3$.Cu(OH)$_2$ (7.87 g, 35.6 mmol)

and DMA (300 mL). This suspension was heated to 120° C. for about 30 minutes (or until greater than 95% conversion was achieved). When formation of the intermediate hydrazone was complete, the hydrazone solution was added to the flask containing the hot suspension of potassium carbonate and CuCO$_3$.Cu(OH)$_2$ over a period of 5 minutes. The flask containing the hydrazone intermediate was washed with DMA (50 mL) and this wash was added to the main reaction flask. Heating at 120° C. was continued for 3.5 hours at which point the level of the hydrazone intermediate was determined to be less than or equal to 1.5 a %. The reaction was cooled to ambient temperature, filtered through GF/F filter paper and washed with isopropyl acetate (500 mL). The filtrate was assayed for 5-fluoro-2-((1-(2-hydroxyethyl)-1H-indazol-5-yl)oxy)benzonitrile and found to contain 76.3 g (86%) of this compound. The filtrate was added to a separatory funnel with further dilution in isopropyl acetate (1000 mL). The isopropyl acetate layer was washed with a mixture of saturated aqueous sodium chloride and 2 M HCl (6:4, 1000 mL) and the phases were separated. The aqueous layer was back extracted with isopropyl acetate (500 mL). The combined isopropyl acetate layers were washed with a mixture of saturated aqueous sodium chloride and 2 N NH$_4$OH (1:1, 1000 mL) and the phases were separated. The isopropyl acetate layer was washed with a mixture of saturated aqueous sodium chloride, 2 M HCl (50:1, 490 mL of brine and 10 mL of 2 M HCl) and the phases were separated. The isopropyl acetate layer was washed with a mixture of saturated aqueous sodium chloride and water (1:4, 500 mL) and the phases were separated. The isopropyl acetate layer was stirred with charcoal (20 g) for 60 minutes. The charcoal was removed via filtration and the cake was washed with isopropyl acetate (170 mL). The filtrate was concentrated under reduced pressure and a suspension began to form. Once the volume was reduced, MTBE (500 mL) was added and the suspension stirred for 2 hours. The product was filtered (polypropylene) and washed with MTBE (200 mL). The solid was dried in a vacuum oven at 55° C. to give 64.6 g of 5-fluoro-2-((1-(2-hydroxyethyl)-1H-indazol-5-yl)oxy)benzonitrile that was 96.1 wt %.

Step (b): Preparation of 2-(5-(2-(aminomethyl)-4-fluorophenoxy)-1H-indazol-1-yl)ethanol To a 8 L Parr reactor was charged Raney Nickel MC700 (Evonik, catalog #48.5198.0000.00; 200 g, about 80 wt % water; the majority of the water was decanted away prior to addition), 5-fluoro-2-((1-(2-hydroxyethyl)-1H-indazol-5-yl)oxy)benzonitrile (400 g, 1311 mmol, 1.0 eq.), MeOH (2850 mL) and 7M NH$_3$ in MeOH (1150 mL, final NH$_3$ concentration about 2 M). The slurry was stirred at 100° C. under hydrogen (200 psi) for 5 hours. The reaction was sampled (5 µL diluted to 1 mL for HPLC analysis) and was determined complete when there was <1% of 5-fluoro-2-((1-(2-hydroxyethyl)-1H-indazol-5-yl)oxy)benzonitrile by HPLC. The mixture was cooled to ambient temperature and filtered through Celite® (545 grade). The reactor was rinsed with MeOH (2×1 L) which was then used to wash the Celite® pad. The filtrate was concentrated to 900 g and diluted with 2-propanol (2 L). The solution was concentrated to 944 g and diluted with 2-propanol (4 L). The mixture was stirred at 45° C. for 15 minutes. The mixture was then filtered and the solids washed with 2-propanol (500 mL). The filtrate was concentrated to 1445 g, and solids precipitated upon concentration. The slurry was transferred to a 12 L round bottom flask with 2-propanol (2×100 mL). The suspension was heated to 60° C. and all of the solids dissolved. Heptane (1200 mL) was added to the slurry maintaining the temperature >50° C. The solution was seeded with 2-(5-(2-(aminomethyl)-4-fluorophenoxy)-1H-indazol-1-yl)ethanol (0.5 g) and then allowed to cool to ambient temperature. Solids formed upon cooling. Heptane (1200 mL) was added and the suspension was stirred at ambient temperature for 15 minutes. Heptane (1200 mL) was added and the suspension was stirred at ambient temperature for 3 hours. The solids were collected by filtration through polypropylene filter cloth (20 µm) and washed with 25% 2-propanol in heptane (1200 mL) in portions. The solids were dried under vacuum at 60° C. yielding 301 g of 2-(5-(2-(aminomethyl)-4-fluorophenoxy)-1H-indazol-1-yl)ethanol.

Example 1A

Alternative Preparation of 5-fluoro-2-((1-(2-hydroxyethyl)-1H-indazol-5-yl)oxy)benzonitrile

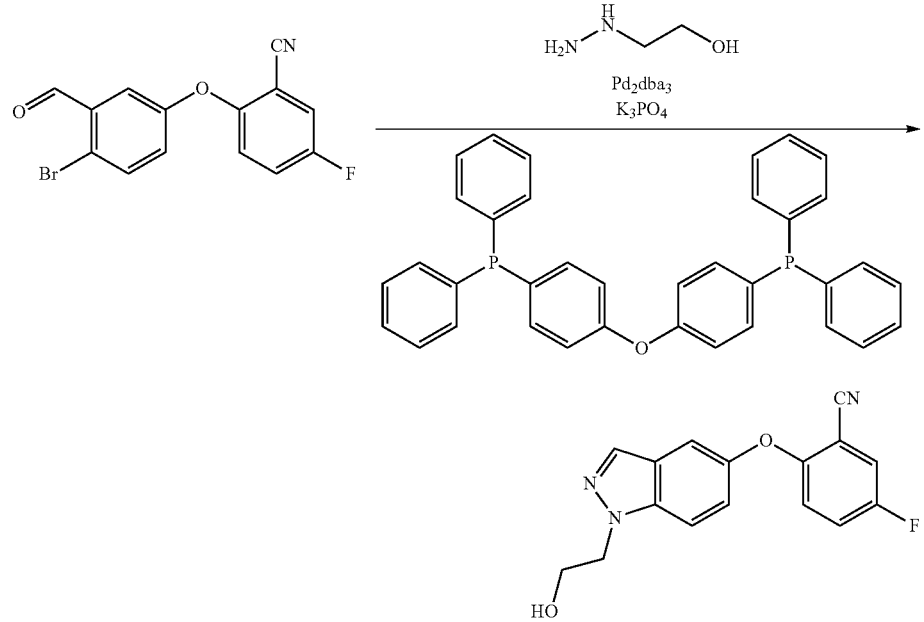

To a round-bottomed flask was added 2-hydrazinylethanol (0.43 mL, 6.25 mmol, 1.0 eq.), 2-(4-bromo-3-formylphenoxy)-5-fluorobenzonitrile (2.0 g, 6.25 mmol, 1.0 eq.), and DMA (30 mL). The mixture was heated to 120° C. for 1 hour. The hydrazone formation was deemed complete when there was less than 5a % of bromo-3-formylphenoxy)-5-fluorobenzonitrile remaining. At that time, potassium phosphate (3.32 g, 15.6 mmol, 2.5 eq.), 4,4'-oxybis(4,1-phenylene)bis(diphenylphosphine) (0.13 g, 0.25 mmol, 0.04 eq.), and tris(dibenzylideneacetone)dipalladium(0) (0.11 g, 0.13 mmol, 0.02 eq.) were added and heating was continued at 120° C. for 20 hours. The reaction was monitored by HPLC. After 5 hours, there was 75a % desired product and 6a % intermediate hydrazone. After 20 hours, there was 1.6a % of the intermediate hydrazone but the desired product had gone down to 64a %. The amount of dimer (a) was higher (8a % after 20 hours reaction time) using palladium catalysis than using when using $CuCO_3Cu(OH)_2$ (Example 1), in which amount the dimer (a) was <0.1a %. The isolated yield of product was not determined.

Example 2

Preparation of phenyl (3-(tert-butyl)-1-(p-tolyl)-1H-pyrazol-5-yl)carbamate

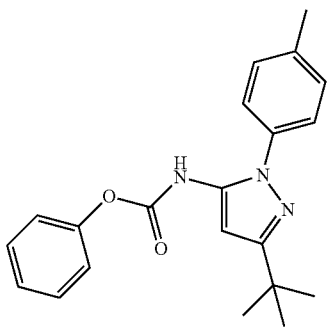 [SMILES: Cc1ccc(-n2nc(C(C)(C)C)cc2NC(=O)Oc2ccccc2)cc1]

Step A: Preparation of 3-(tert-butyl)-1-(p-tolyl)-1H-pyrazol-5-aminium chloride

A reactor was equipped with mechanical stirrer, temperature probe, heating mantle, reflux condenser and $N_2$ adaptor for positive $N_2$ pressure. The flask was charged with 2-(p-tolyl)hydrazin-1-ium chloride (100 g, 630.4 mmol, 1.0 equivalents) followed by 4,4-dimethyl-3-oxopentanenitrile (86.8 g, 693.4 mmol, 1.1 eq.). To the stirring solids was charged MeOH (500 mL), and the mixture was warmed to reflux until HPLC confirmed the reaction was complete (>99.5%; 200-fold dilution, 10 µL in 2.0 mL MeOH, 5 µL injection). The reaction mixture was cooled and then concentrated to 300 mL. Once the target volume was obtained, the mixture was warmed to >50° C. and MTBE (1 L) was added to form a slurry. The slurry was cooled to ambient temperature (25+/−5° C.) and was allowed to remain at this temperature for at least 30 minutes. The product was collected by filtration and washed with MTBE (800 mL). The crude solid was transferred to vacuum oven and dried at 50° C. under high vacuum until constant weight was achieved. This gave crude 3-(tert-butyl)-1-(p-tolyl)-1H-pyrazol-5-aminium chloride (158 g, 94% yield).

Step B: Preparation of phenyl (3-(tert-butyl)-1-(p-tolyl)-1H-pyrazol-5-yl)carbamate A flask was charged with 3-(tert-butyl)-1-(p-tolyl)-1H-pyrazol-5-aminium chloride (20.00 g, 75.25 mmol) followed by isopropyl acetate (260 mL) and phenyl chloroformate (13.20 mL, 105.3 mmol, 1.4 eq.). A separate vessel was charged with potassium carbonate (10.40 g, 75.25 mmol, 1.0 eq.) followed by deionized water (40 mL). The slurry was stirred until dissolution of the potassium carbonate was complete. The resulting aqueous potassium carbonate solution was added to the slurry of 3-(tert-butyl)-1-(p-tolyl)-1H-pyrazol-5-aminium chloride while maintaining the temperature at 20-21° C. The mixture was stirred at 23-24° C. overnight (for convenience, reaction generally complete within 4 hours). After stirring the biphasic slurry overnight, analysis by HPLC showed complete conversion, and the phases were allowed to settle for 45 minutes. The phases were separated and the isopropyl acetate layer was washed with water (40 mL). The phases were allowed to settle and then the aqueous layer was removed. The isopropyl acetate solution was concentrated to 40 mL under vacuum with heating up to 40° C. and a suspension formed. The suspension was heated to 50±5° C. and heptane (200 mL) was added while maintaining the temperature at 50±5° C. The suspension was held at this temperature for 1.5 hours and then cooled to ambient temperature over 2 hours and then stirred overnight. The product was isolated by filtration and washed with heptane (2×40 mL). The wet cake was dried under vacuum to constant weight to give 24.88 g (94.6% yield, 100a %) of phenyl (3-(tert-butyl)-1-(p-tolyl)-1H-pyrazol-5-yl)carbamate.

Example 3

Preparation of 1-(3-tert-butyl-1-p-tolyl-1H-pyrazol-5-yl)-3-(5-fluoro-2-(1-(2-hydroxyethyl)-1H-indazol-5-yloxy)benzyl)urea (Compound A) and HCl Salt Formation

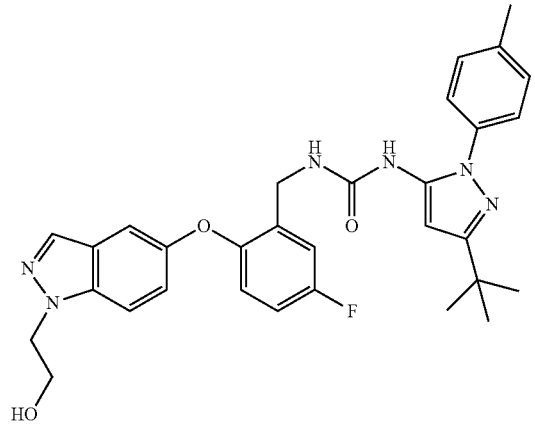 [SMILES: Cc1ccc(-n2nc(C(C)(C)C)cc2NC(=O)NCc2cc(F)ccc2Oc2ccc3c(cnn3CCO)c2)cc1]

2-(5-(2-(Aminomethyl)-4-fluorophenoxy)-1H-indazol-1-yl)ethanol (12.13 kg, 40.27 mol) and phenyl (3-(tert-butyl)-1-(p-tolyl)-1H-pyrazol-5-yl)carbamate (14.00 kg, 40.07 mol) were charged to a glass lined reactor. The solids were suspended in 2-propanol (220 L). The suspension was heated to 35° C. and stirred at 35-40° C. The solids went into solution once heated. After 5 hours, IPC HPLC showed complete conversion. The reaction mixture was cooled to 25° C. and subsequently polish filtered and rinsed with 2-propanol (14 L). To the filtered solution was added HCl (4.80 kg of 32% aqueous HCl, 1.05 eq.) through a polish filter at 22-23° C. The mixture was stirred at 18-23° C. overnight, at which time the expected crystallization had not occurred. The reaction mixture was then seeded with Compound A previously prepared on a smaller scale (20.0 g of Compound A were suspended in 300-400 mL of 2-propanol and added to the reaction mixture). This mixture was stirred for up to 3 days. The suspension was sampled and the mother liquor was analyzed for Compound A. Results showed complete crystallization (6.7 mg/mL of Compound A in the filtrate) and Compound A was isolated by filtration. Compound A was washed with 2-propanol (81.4 L) added through a polish filter in portions. The product was dried under vacuum at 55° C. for 28.5 hours. The dry product was homogenized with a quadro comill utilizing a sieve with screen opening size of 3.1 mm to provide 21.93 kg of Compound A HCl Salt (92.3% yield, 99.6a %).

Example 4

Alternative Preparation of 2-(4-bromo-3-formylphenoxy)-5-fluorobenzonitrile

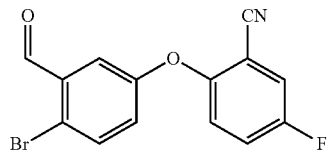 [SMILES: N#Cc1cc(F)ccc1Oc1ccc(Br)c(C=O)c1]

2-Bromo-5-hydroxybenzaldehyde (20.0 g, 99.5 mmol, 1.0 eq.), ethanol (100 mL), triethoxymethane (20 mL, 120 mmol, 1.2 eq.) and ammonium chloride (0.286 g, 5.3 mmol, 0.05 eq.) were combined in a round bottom flask. The reaction was stirred at 40° C. for 1 hour and was then allowed to cool to <35° C. Dimethylacetamide (100 mL) was added and the reaction mixture was concentrated under vacuum until ethanol was about 10 wt % of the solution by GC analysis. The reaction mixture was then transferred to a round bottom flask containing 2,5-difluorobenzonitrile (12.46 g, 89.54 mmol, 0.9 eq.), potassium carbonate (16.50 g, 119.4 mmol, 1.2 eq.) and dimethylacetamide (25 mL). The reaction mixture was warmed to 100° C. and stirred for 23 hours. The reaction mixture was allowed to cool to ambient temperature and then filtered through a polypropylene cloth filter. The solids were washed with tetrahydrofuran (100 mL). The combined filtrates were transferred to a round bottom flask with tetrahydrofuran (25 mL). 2 M aqueous hydrochloric acid (200 mL) was added and the reaction mixture was stirred at 40° C. for 3 hours. The reaction mixture was cooled to less than 30° C. and transferred to a separatory funnel with ethyl acetate (200 mL). After mixing, the aqueous layer was removed and the organic layer was washed with 1 M aqueous sodium hydroxide (2×100 mL) and saturated aqueous sodium chloride (100 mL). The organic layer was concentrated and 2-propanol (200 mL) was added. The solution was again concentrated and 2-propanol (100 mL) was added. The solution was concentrated and heptane (30 mL) was added. The mixture was heated to 30° C. for 30 minutes and then allowed to cool to ambient temperature. After stirring for 1 hour the slurry was filtered through a polypropylene filter cloth and the solids were washed with 1:1 2-propanol:heptane (100 mL) The solids were dried under vacuum at 55° C. yielding 22.67 g of 2-(4-bromo-3-formylphenoxy)-5-fluorobenzonitrile that was 99 wt %.

Example 5

Alternative Procedure for the Preparation of 2-(5-(2-(aminomethyl)-4-fluorophenoxy)-1H-indazol-1-yl)ethanol

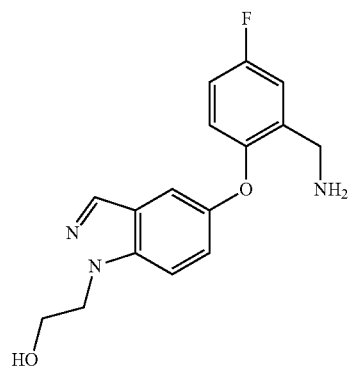 [SMILES: N=Cc1cc(Oc2ccc(F)cc2CN)ccc1NCCO]

5-Fluoro-2-((1-(2-hydroxyethyl)-1H-indazol-5-yl)oxy)benzonitrile (303.1 g, 1.0 eq.) was combined with MC703 slurry (150 g, 80% water) and 2M NH$_3$ in IPA (4.5 L, 15 mL/g) and heated to 100° C. under 200 psi H$_2$ in an 8 L Parr vessel. After 8 hours, the reaction was cooled to ambient temperature and allowed to stand for 12 hours. The slurry was transferred to a carboy with IPA (600 mL, 2 mL/g) and filtered through Celite®. The Celite® bed was washed with IPA (2×600 mL/g, 4 mL/g total). The filtrate was concentrated to 1200 mL (4 vol) under vacuum and allowed to cool to ambient temperature. After stirring for 12 hours, heptane was added (2700 mL, 9 mL/g) and the mixture was stirred for 4 hours. The solids were collected by filtration and washed with 3:1 heptane:IPA (2×600 mL, 4 mL/g total). The solids were dried under vacuum at 60° C. yielding 243.8 g of the title compound.

Example 6

Alternate Preparation of 2-(4-bromo-3-formylphenoxy)-5-fluorobenzonitrile

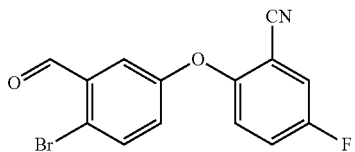 [SMILES: N#Cc1cc(F)ccc1Oc1ccc(Br)c(C=O)c1]

To a solution of 2-bromo-5-hydroxybenzaldehyde (5.0 g, 25 mmol, 1.0 eq) and 2,5-difluorobenzonitrile (6.9 g, 50 mmol, 2.0 eq) in DMSO (25 mL) was added K$_2$CO$_3$ 325 mesh (2.4 g, 17 mmol, 0.70 eq). The mixture was warmed to 80° C. for 19 hours, after which the reaction was determined to be ≥99.5 a % complete by HPLC. The heat source was removed and the reaction was cooled to ambient temperature. CH$_3$CN (40 mL, 8 mL/g) and water (40 mL, 8 mL/g) were added. The mixture was allowed to stir at ambient temperature for 20 hours and the solids were removed by filtration, washed with 1:1 CH$_3$CN:water (2×2 mL/g), and dried to give 5.95 g (75%) of the title product. Loss to filtrate was calculated to be 1.2 g (15%). Solid was 98.8a % pure and 99.7 wt %.

Representative Example A

Preparation of methyl 2-(5-(2-cyano-4-fluorophenoxy)-1H-indazol-1-yl)acetate and methyl 2-(5-(2-cyano-4-fluorophenoxy)-2H-indazol-2-yl)acetate

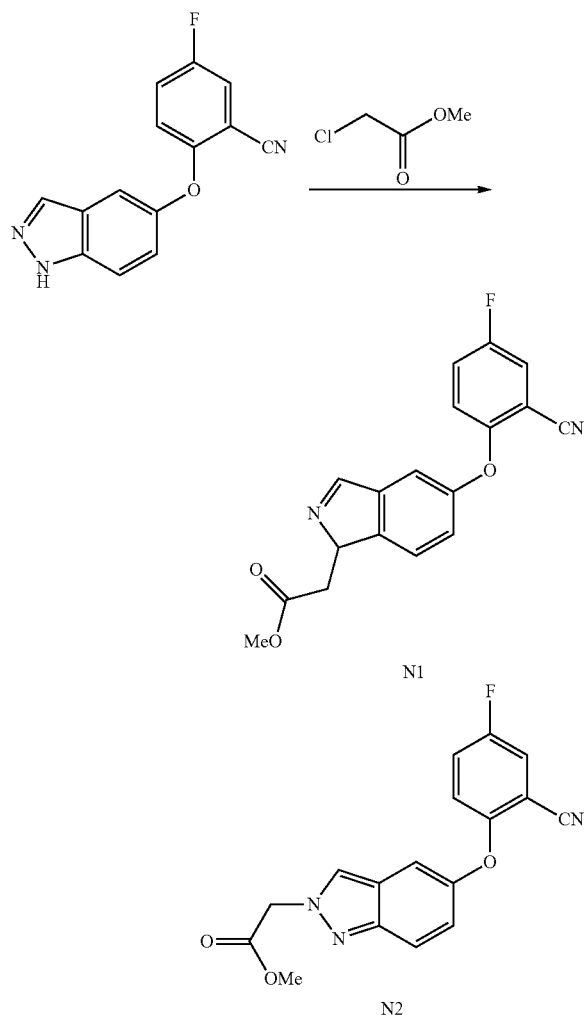

To a round bottom flask under N$_2$ atmosphere was added 2-((1H-indazol-5-yl)oxy)-5-fluorobenzonitrile (2300 g, 9.08 mole), K$_2$CO$_3$ (1883 g, 13.6 mol) and tetrabutylammonium iodide (335 g, 0.91 mol). To the solid was added DMF (23 L) and methyl chloroacetate (1479 g, 13.6 mol) and the mixture was heated to an internal temperature of 65° C. with mechanical stirring. After 24 hours additional methyl chloroacetate (296 g, 2.73 mol) and K$_2$CO$_3$ (377 g, 2.73 mol) were added. After 32 hours the internal temperature was raised to 70° C. and additional methyl chloroacetate (65 g, 0.595 mol) and K$_2$CO$_3$ (141 g, 1.02 mol) were added. After 48 hours additional methyl chloroacetate (100 g, 0.915 mol) and K$_2$CO$_3$ (125 g, 0.905 mol) were added, and then after 56 hours additional methyl chloroacetate (100 g, 0.915 mol) and K$_2$CO$_3$ (125 g, 0.905 mol) were added. After 72 hours the reaction was called complete even though the amount of the N2-substituted derivative was still >5% and the conversion of the N2-substituted derivative to the N1-substituted derivative had stalled. After the reaction was cooled to near ambient temperature the solids were removed by filtration and the filtrate was transferred to a second flask containing water (57.5 L). The resulting suspension was allowed to stir for 2 hours and then collected via filtration. The flask and cake were washed with water (23 L). A final heptane (10 L) wash of the cake was performed. The solid was then transferred to an oven and dried under vacuum at 55-60° C. until constant weight was achieved (2886 g crude). The crude solid was recrystallized (ethyl acetate/heptane) with two other batches of product to deliver the final product in 78.4% yield.

The above reaction was performed on four different scales. Table A shows the amount of the N2-derivative in the crude reaction mixture.

TABLE A

| Run # | Scale (amount of 2-((1H-indazol-5-yl)oxy)-5-fluorobenzonitrile) | Amount of N2-substituted derivative |
|---|---|---|
| 1 | 50 g | 0.8% |
| 2 | 1423 g | 3.3% |
| 3 | 2258 g | 3.0% |
| 4 | 2300 g | 5.3% |

Representative Example B

Preparation of 2-(5-(2-(aminomethyl)-4-fluorophenoxy)-1H-indazol-1-yl)ethanol

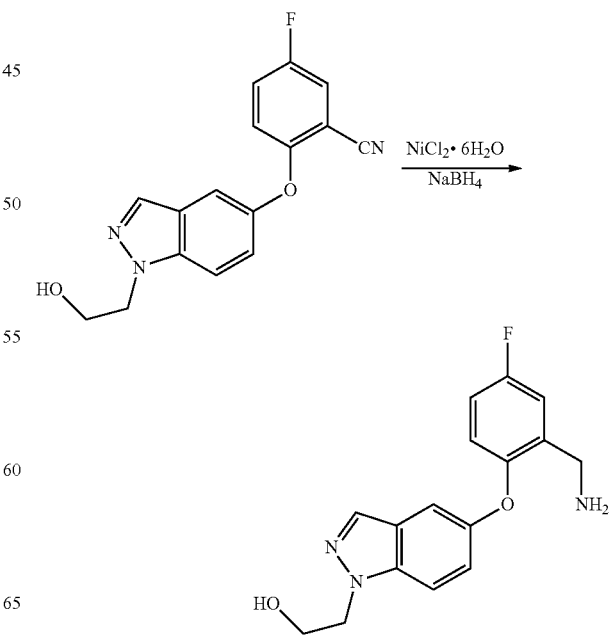

To a round bottom flask under a N₂ atmosphere was added 5-fluoro-2-((1-(2-hydroxyethyl)-1H-indazol-5-yl)oxy)benzonitrile (1523 g, 5.13 mole) ethanol (22.8 L) and methanol (22.8 L). The mixture was mechanically stirred and cooled to <5° C. (internal temperature). Nickel chloride hexahydrate (226 g, 0.51 mol) was added, and then the first portion of sodium borohydride (343 g, 14.9 mol) was added. The temperature rose to 14.4° C. and then stabilized, at which point a second portion of sodium borohydride (337 g, 14.7 mol) was added. The temperature rose to 16.9° C. and then stabilized, at which point the final portion of sodium borohydride (211 g, 9.18 mol) was added, and the reaction was stirred for 2.5 hours. To the mixture was added Darko G-60 (309 g, 20 wt %), saturated Na₂CO₃ (31.7 kg) and methanol (7.95 L). After 1 hour the mixture was filtered through GF/F media. The flask and cake were washed with methanol (5 L). The filtrate was concentrated under vacuum at 40° C. When the volume of the reaction mixture was reduced to 30 L the reactor was charged with water (4 L) and the concentration continued until the volume of the reaction mixture was again reduced to about 30 L. The concentrate was assayed and found to contain 1220 g of 2-(5-(2-(aminomethyl)-4-fluorophenoxy)-1H-indazol-1-yl)ethanol and was 91.8 area % pure by HPLC. The amount of "diol (e)" was about 1.0a %, the amount of "dimer (b)" was about 1.8a %, the amount of "des-fluoro impurity (d)" was about 0.18a % and the amount of "dimer (c)" was about 0.22a % by HPLC (see Table B).

To the concentrate was added isopropyl acetate (21.2 L) and sodium chloride (38.1 kg). The mixture was stirred for 10 minutes and then transferred to a separatory funnel. With the mixture stirring, 50% sodium hydroxide (1523 mL) was added. The mixture was stirred for 10 minutes and then the phases were allowed to dissipate. The aqueous layer was removed and the organic layer was washed with saturated brine (12.8 kg). The aqueous layer was removed and the organic layer was washed with 0.05 M citric acid (30.7 L). The organic layer was removed. To the aqueous layer was added isopropyl acetate (24.4 L) and the mixture was stirred. To the stirred solution was added 50% NaOH (1.5 L) and after 3 minutes the phases were allowed to dissipate. The phases were separated and the organic layer was washed with saturated brine (13.5 kg). The phases were separated and the organic layer was concentrated under vacuum. To the concentrated residue was added dichloromethane (4.8 L) and the solution was added to a reactor. Additional dichloromethane (225 g) was added and then heptane (3297 g) was slowly added to produce a solid. The solid was collected via filtration, and the flask and cake were washed with 2:1 heptane/dichloromethane. The solid was dried in a vacuum oven at 55° C. until a constant weight was achieved. The dried solid weighed 1163 g and was 99.6 area % pure by HPLC. The amount of "diol (e)" was <0.05a %, the amount of "dimer (b)" was <0.05a %, the amount of "dimer (c)" was 0.16a % and the amount of "des-fluoro impurity (c)" was 0.10a % by HPLC (see Table B).

TABLE B

| Crude Filtrate (HPLC area %) | Isolated Yield (HPLC area %) |
|---|---|
| Formula I: 91.8% | Formula I: (99.6%) |
| Diol (e): 1.0% | Diol (e): <0.05% |
| dimer (b): 1.8% | Dimer (b): <0.05% |
| dimer (c): 0.22% | dimer (c): 0.16% |
|  | des-Fluoro (d): 0.11% |

What is claimed is:

1. A process for the preparation of a compound of formula I

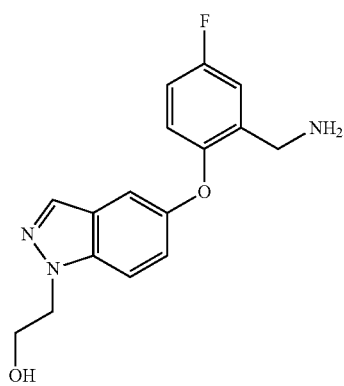

comprising:

(a) reacting a compound of formula (2)

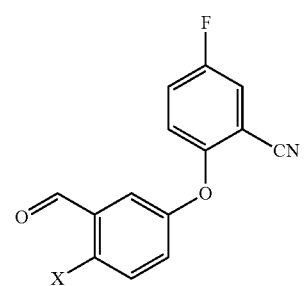

where X is Br or I, with 2-hydrazinylethanol in the presence of a base and a transition metal catalyst to provide a compound of formula (3)

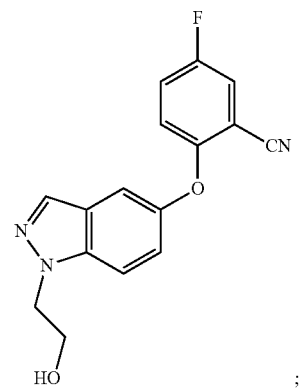

and (b) reducing the nitrile group of compound (3) to provide said compound of Formula I.

2. The process of claim 1, wherein the compound of formula (2) is prepared by the process comprising:
(a1) reacting a compound of formula (1)

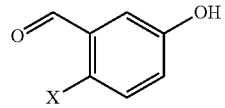

where X is Br or I, with 2,5-difluorobenzonitrile in the presence of a base to provide said compound of formula (2).

3. The process of claim 2, wherein about two equivalents of 2,5-difluorobenzonitrile are used.

4. The process of claim 3, wherein said base in step (a1) is an alkali metal carbonate, an alkali metal hydride or an alkali metal bicarbonate.

5. The process according to claim 4, wherein about 1.05 to about 1.2 equivalents of 2-hydrazinylethanol are used.

6. The process according to claim 5, wherein the base in step (a) is an alkali metal carbonate, an alkali metal phosphate, an alkali metal hydride, an alkali metal alkoxide, or an alkali metal hydroxide.

7. The process according to claim 6, wherein the transition metal catalyst is a copper, platinum, palladium, iron, nickel, ruthenium or rhodium catalyst.

8. The process according to claim 7, wherein the transition metal catalyst is a copper catalyst.

9. The process according to claim 8, wherein the copper catalyst is $CuCO_3 \cdot Cu(OH)_2$, CuI, CuO, $CuBr_2$, $CuCO_3$, CuCl or $Cu_2O$.

10. The process according to claim 9, wherein the copper catalyst is $CuCO_3 \cdot Cu(OH)_2$.

11. The process according to claim 10, wherein the reaction is performed in the absence of a diamine ligand.

12. The process according to claim 11, wherein about 0.20 to 0.25 equivalents of the transition metal catalyst is used.

13. The process according to claim 12, wherein the nitrile group of compound (3) is reduced under catalytic hydrogenation conditions.

14. The process of claim 13, wherein said catalytic hydrogenation conditions comprise treating compound (3) with a Raney nickel catalyst in the presence of ammonia and hydrogen.

15. The process of claim 14, wherein said Raney nickel catalyst is Raney Ni-MC700 or Raney Ni-MC703.

16. The process of claim 15, wherein said product contains less than 0.10 a % by HPLC of the impurity (2,2'-(5,5'-(((azanediylbis(methylene))bis(4-fluoro-2,1-phenylene))bis(oxy))bis(1H-indazole-5,1-diyl))diethanol).

17. The process of claim 15, wherein said product contains less than 0.10 a % by HPLC of the impurity 2,2'-(5,5'-(((1,2-diaminoethane-1,2-diyl)bis(4-fluoro-2,1-phenylene))bis(oxy))bis(1H-indazole-5,1-diyl))diethanol).

18. The process of claim 15, wherein said product contains less than 0.10 a % by HPLC of the impurity 2-(5-(2-(aminomethyl)phenoxy)-1H-indazol-1-yl)ethanol).

19. The process of claim 15, wherein said product contains less than 0.10 a %, by HPLC, of the impurity 2-(5-(4-fluoro-2-(hydroxymethyl)phenoxy)-1H-indazol-1-yl)ethanol).

20. A process for preparing a Compound (A) having the formula

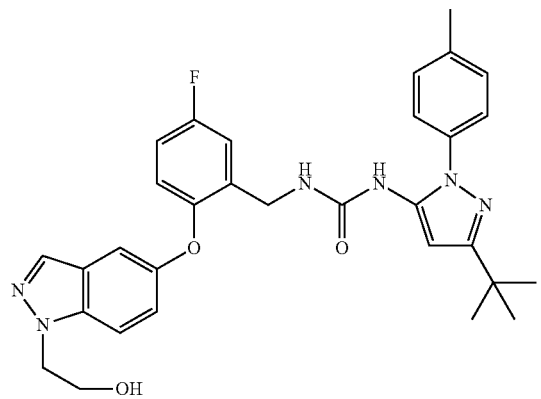 [SMILES: Cc1ccc(-n2nc(C(C)(C)C)cc2NC(=O)NCc2cc(F)ccc2Oc2ccc3c(cnn3CCO)c2)cc1]

comprising:
(a) reacting a compound of formula (2)

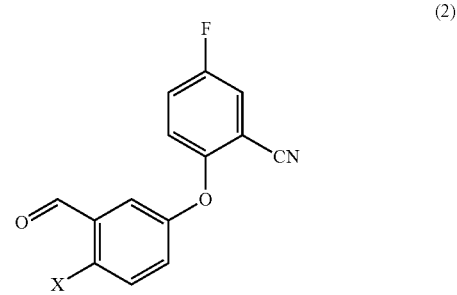

where X is Br or I, with 2-hydrazinylethanol in the presence of a base and a transition metal catalyst to provide a compound of formula (3)

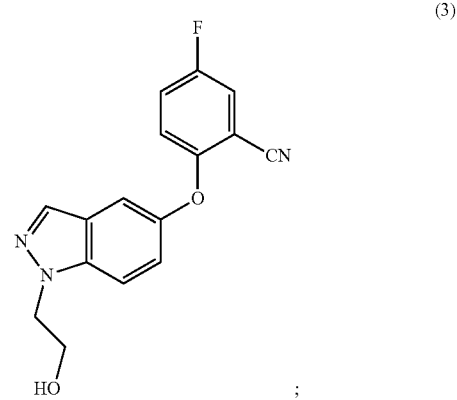 [SMILES: N#Cc1cc(F)ccc1Oc1ccc2c(cnn2CCO)c1]

(b) reducing the nitrile group of compound (3) to provide a compound of Formula I

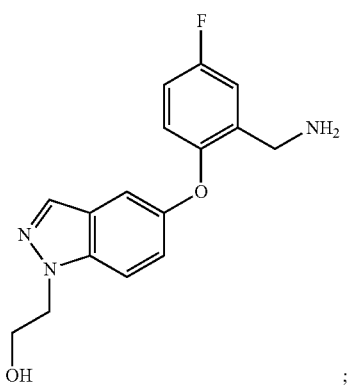

(c) coupling said compound of Formula I with a compound of formula (4)

(4)

where Z represents a leaving group, to provide said Compound (A); and (e) optionally treating the product of Step (d) with HCl to isolate Compound (A) as the monohydrochloride salt.

21. The process of claim 20, wherein the compound of formula (2) is prepared by the process comprising:
(a1) reacting a compound of formula (1)

(1)

where X is Br or I, with 2,5-difluorobenzonitrile in the presence of a base to provide said compound of formula (2).

22. The process of claim 21, wherein about two equivalents of 2,5-difluorobenzonitrile are used.

23. The process of claim 22, wherein said base in step (a1) is an alkali metal carbonate, an alkali metal hydride or an alkali metal bicarbonate.

24. The process according to claim 23, wherein about 1.05 to about 1.2 equivalents of 2-hydrazinylethanol are used.

25. The process according to claim 24, wherein the base in step (a) is an alkali metal carbonate, an alkali metal phosphate, an alkali metal hydride, an alkali metal alkoxide, or an alkali metal hydroxide.

26. The process according to claim 25, wherein the transition metal catalyst is a copper, platinum, palladium, iron, nickel, ruthenium or rhodium catalyst.

27. The process according to claim 26, wherein the transition metal catalyst is a copper catalyst.

28. The process according to claim 27, wherein the copper catalyst is $CuCO_3.Cu(OH)_2$, CuI, CuO, $CuBr_2$, $CuCO_3$, CuCl or $Cu_2O$.

29. The process according to claim 28, wherein the copper catalyst is $CuCO_3.Cu(OH)_2$.

30. The process according to claim 29, wherein step (a) is performed in the absence of a diamine ligand.

31. The process according to claim 30, wherein about 0.20 to 0.25 equivalents of the transition metal catalyst are used.

32. The process according to claim 31, wherein the nitrile group of compound (3) is reduced under catalytic hydrogenation conditions.

33. The process of claim 32, wherein said catalytic hydrogenation conditions comprise treating compound (3) with a Raney nickel catalyst in the presence of ammonia and hydrogen.

34. The process of claim 33, wherein said Raney nickel catalyst is Raney Ni-MC700 or Raney Ni-MC703.

35. The process according to claim 34, wherein the leaving group represented by Z is a halo(1-6C)alkoxy group, an alkenyloxy group, or an aryloxy group wherein the aryl portion is optionally substituted with one or more groups independently selected from F, Cl, Br, and $NO_2$.

* * * * *

UNITED STATES PATENT AND TRADEMARK OFFICE
CERTIFICATE OF CORRECTION

PATENT NO. : 9,790,206 B2
APPLICATION NO. : 14/770035
DATED : October 17, 2017
INVENTOR(S) : C. Todd Eary et al.

It is certified that error appears in the above-identified patent and that said Letters Patent is hereby corrected as shown below:

In the Claims

Column 37, Line 56, Claim 16, please delete "less than 0.10 a%" and insert -- less than 0.10 % --;

Column 37, Line 61, Claim 17, please delete "less than 0.10 a%" and insert -- less than 0.10 % --;

Column 37, Line 65, Claim 18, please delete "less than 0.10 a%" and insert -- less than 0.10 % --;

Column 38, Line 2, Claim 19, please delete "less than 0.10 a%" and insert -- less than 0.10 % -- therefor.

Signed and Sealed this
Fifteenth Day of May, 2018

Andrei Iancu
*Director of the United States Patent and Trademark Office*